(12) United States Patent
Imamura et al.

(10) Patent No.: US 10,806,412 B2
(45) Date of Patent: Oct. 20, 2020

(54) RADIOGRAPHY SYSTEM AND METHOD FOR OPERATING RADIOGRAPHY SYSTEM

(71) Applicant: FUJIFILM Corporation, Tokyo (JP)

(72) Inventors: Ryo Imamura, Ashigarakami-gun (JP);
Koichi Kitano, Ashigarakami-gun (JP);
Naoyuki Nishino, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 16/059,276

(22) Filed: Aug. 9, 2018

(65) Prior Publication Data

US 2019/0046134 A1 Feb. 14, 2019

(30) Foreign Application Priority Data

Aug. 10, 2017 (JP) .................................. 2017-156063

(51) Int. Cl.
*A61B 6/00* (2006.01)
*A61B 6/02* (2006.01)
(Continued)

(52) U.S. Cl.
CPC .......... *A61B 6/4028* (2013.01); *A61B 6/4283* (2013.01); *A61B 6/4405* (2013.01);
(Continued)

(58) Field of Classification Search
CPC ... A61B 6/4028; A61B 6/4283; A61B 6/4405; A61B 6/464; A61B 6/563; A61B 6/022;
(Continued)

(56) References Cited

U.S. PATENT DOCUMENTS

| 5,539,798 A | * | 7/1996 | Asahina | ................ | A61B 6/022 |
| | | | | | 348/E5.086 |
| 10,111,642 B2 | | 10/2018 | Deinlein et al. | | |

(Continued)

FOREIGN PATENT DOCUMENTS

| DE | 102015211057 A1 | 12/2016 |
| JP | 6-217973 A | 8/1994 |

(Continued)

OTHER PUBLICATIONS

Japanese Office Action, dated Jul. 28, 2020, for corresponding Japanese Application No. 2017-156063, with an English translation.

*Primary Examiner* — Taeho Jo
(74) *Attorney, Agent, or Firm* — Birch, Stewart, Kolasch & Birch, LLP

(57) ABSTRACT

A position detection unit is disposed at an exposure position that is included in a camera image and a field of view of a camera and outputs a position signal indicating the position of a part of a peripheral portion of an electronic cassette. The calculation unit calculates an in-image cassette position which is the position of the electronic cassette in the camera image, on the basis of the position, direction, and size of the position detection unit in the camera image and the position signal. A composite image generation unit generates a composite image of the camera image and a cassette frame indicating the in-image cassette position. A display controller displays the composite image on a touch panel.

21 Claims, 21 Drawing Sheets

(51) Int. Cl.
  *A61B 6/08* (2006.01)
  *A61B 5/00* (2006.01)
(52) U.S. Cl.
  CPC .............. *A61B 6/464* (2013.01); *A61B 6/465* (2013.01); *A61B 6/467* (2013.01); *A61B 6/547* (2013.01); *A61B 6/563* (2013.01); *A61B 5/0077* (2013.01); *A61B 6/022* (2013.01); *A61B 6/08* (2013.01); *A61B 6/4233* (2013.01); *A61B 6/469* (2013.01); *A61B 6/587* (2013.01); *A61B 6/588* (2013.01)
(58) Field of Classification Search
  CPC ......... A61B 6/08; A61B 6/4233; A61B 6/469; A61B 6/587; A61B 6/588
  USPC .......................................................... 378/62
  See application file for complete search history.

(56) References Cited

U.S. PATENT DOCUMENTS

| | | | | |
|---|---|---|---|---|
| 2002/0012450 | A1* | 1/2002 | Tsujii | H05G 1/60 382/103 |
| 2011/0013752 | A1* | 1/2011 | Takahashi | A61B 6/583 378/205 |
| 2012/0018641 | A1* | 1/2012 | Watanabe | A61B 6/563 250/354.1 |
| 2012/0126124 | A1* | 5/2012 | Nakatsugawa | G01T 1/2018 250/363.01 |
| 2012/0126129 | A1* | 5/2012 | Nakatsugawa | G01T 1/20 250/369 |
| 2012/0133339 | A1* | 5/2012 | Eguchi | A61B 6/00 320/162 |
| 2013/0114793 | A1 | 5/2013 | Ohta et al. | |
| 2014/0177804 | A1* | 6/2014 | Kobayashi | A61B 6/54 378/98 |
| 2014/0275954 | A1* | 9/2014 | Ohta | A61B 1/00006 600/407 |
| 2015/0055752 | A1* | 2/2015 | Takahashi | H04N 5/32 378/62 |
| 2015/0055753 | A1* | 2/2015 | Tajima | A61B 6/08 378/62 |
| 2015/0276944 | A1* | 10/2015 | Enomoto | G01T 1/175 378/101 |
| 2016/0089092 | A1* | 3/2016 | Shimizukawa | A61B 6/54 378/98 |
| 2016/0174918 | A1* | 6/2016 | Wang | A61B 6/588 378/63 |
| 2017/0135667 | A1* | 5/2017 | Becker | A61B 6/4464 |
| 2017/0172536 | A1 | 6/2017 | Song et al. | |
| 2017/0219498 | A1* | 8/2017 | Chtcheprov | G01N 23/046 |

FOREIGN PATENT DOCUMENTS

| | | |
|---|---|---|
| JP | 2010-119485 A | 6/2010 |
| JP | 2012-024399 A | 2/2012 |
| JP | 2016-209548 A | 12/2016 |

* cited by examiner

| IMAGE ID | IF0001 |
| --- | --- |
| IMAGING DATE AND TIME | 7/10/2017 11:05 |
| SUBJECT ID | H0500 |
| NAME | ○○○○ |
| SEX | MALE |
| DATE OF BIRTH | 09/25/1985 |
| AGE | 28 |
| HEIGHT | 183 |
| WEIGHT | 78 |
| ORDER ID | OD0001-A |
| IMAGING MENU | CHEST, DECUBITUS POSITION, FRONT |
| TUBE VOLTAGE | 100 |
| TUBE CURRENT | 200 |
| IRRADIATION TIME | 20 |

FIG. 9

| ORDER ID | SUBJECT ID | ROOM NUMBER | IMAGING COMPLETION STATE | CASSETTE ID | IMAGING MENU | IRRADIATION CONDITIONS | IMAGE ID |
|---|---|---|---|---|---|---|---|
| OD0001-A | H0500 | 201 | COMPLETED | DR0001 | CHEST, DECUBITUS POSITION, FRONT | TUBE VOLTAGE: 100kV… | IF0001 |
| OD0001-B | H0500 | 201 | COMPLETED | DR0002 | ABDOMEN, DECUBITUS POSITION, FRONT | TUBE VOLTAGE: 150kV… | IF0002 |
| OD0002 | H0600 | 202 | NOT CAPTURED | DR0003 | CHEST, DECUBITUS POSITION, FRONT | TUBE VOLTAGE: 100kV… | - |

78

RADIOGRAPHY SYSTEM AND METHOD FOR OPERATING RADIOGRAPHY SYSTEM

CROSS-REFERENCE TO RELATED APPLICATION

This application claims priority under 35 USC 119 from Japanese Patent Application No. 2017-156063, filed 10 Aug. 2017, the disclosure of which is incorporated by reference herein.

BACKGROUND OF THE INVENTION

1. Field of the Invention

The present invention relates to a radiography system and a method for operating the radiography system.

2. Description of the Related Art

In a medical field, a diagnosis is made on the basis of a radiographic image obtained by a radiography system. The radiography system includes a radiation generation apparatus and a radiography apparatus. The radiation generation apparatus includes a radiation source and the radiography apparatus includes a radiographic image detection device. The radiographic image detection device includes a sensor panel. The sensor panel is provided with an imaging region. A plurality of pixels are two-dimensionally arranged in the imaging region. The pixel is sensitive to radiation which has been emitted from the radiation source and then transmitted through a subject (patient) and accumulates charge. The radiographic image detection device converts the charge accumulated in the pixel into a digital signal and outputs the digital signal as a radiographic image.

The radiographic image detection devices are classified into a fixed type that is fixed to an imaging stand installed in an imaging room and a portable type in which, for example, a sensor panel is accommodated in a portable housing. The portable radiographic image detection device is referred to as an electronic cassette. The electronic cassettes are classified into a wired type that is supplied with power from a commercial power supply through a cable and a wireless type that is supplied with power from a battery provided in a housing.

The electronic cassette is carried out of the imaging room and is then used since it has high mobility. For example, the electronic cassette is used for visit imaging in which an operator visits a hospital room in which a patient who is not able to move to the imaging room is present and takes a radiographic image. In addition, the electronic cassette is used in places other than medical facilities in order to capture a radiographic image of an aged person who gets medical treatment at home or a patient who is in an emergency situation due to an accident or a disaster. Hereinafter, imaging without using an imaging stand is referred to as free imaging.

In a preparation operation before radiography, an operator, such as a radiology technician, relatively positions a radiation source, an electronic cassette, and a patient. After positioning is completed, the operator operates the radiation source to emit radiation and takes a radiographic image.

JP2012-024399A (corresponding to US2013/114793A1) discloses a technique which supports positioning during free imaging, using an image (hereinafter, a camera image) captured by an optical web camera that is attached to a radiation source. Specifically, the web camera captures an image of a patient and an electronic cassette. Then, the obtained camera image is displayed on a display unit. The operator instructs the patient such that an imaging part of the patient is located at a predetermined position in guide lines (a rectangular frame indicating an imaging region of a sensor panel) drawn in the housing of the electronic cassette while seeing the camera image.

In addition, JP1994-217973A (JP-H06-217973A, corresponding to U.S. Pat. No. 5,539,798A) discloses a technique which does not use an electronic cassette, but uses a film cassette, and supports relative positioning between a patient and the film cassette on the basis of a camera image captured by a television (TV) camera attached to a radiation source. Specifically, the TV camera is used to capture an image of the patient. Then, a composite image of the obtained camera image and a film frame which is an index indicating the position of the film cassette in the camera image is displayed on a display unit. The operator instructs the patient such that an imaging part of the patient is located at a predetermined position in the film frame while seeing the composite image. However, unlike JP2012-024399A, JP1994-217973A (JP-H06-217973A) does not relate to free imaging, but relates to imaging using an imaging stand.

In JP1994-217973A (JP-H06-217973A), the film frame is obtained by capturing the image of the film cassette in the same field of view as that in a case in which radiography is actually performed, using the camera, in a state in which the patient is absent. Alternatively, the film frame is obtained by performing calculation on the basis of the size of a film or a source image distance (SID) which is the distance between a focal position of a radiation tube of the radiation source and an imaging region of a sensor panel.

SUMMARY OF THE INVENTION

In free imaging, an electronic cassette is inserted between a patient and a bed. Therefore, in some cases, the electronic cassette is covered by the patient. In JP2012-024399A, positioning is performed on the basis of the camera image including the patient and the electronic cassette. However, in a case in which the electronic cassette is covered by the patient, the electronic cassette is not included in the camera image. Therefore, the position of the electronic cassette is not known from the camera image. In this case, it is difficult to perform positioning on the basis of the camera image.

In JP1994-217973A (JP-H06-217973A), the composite image of the camera image and the film frame is displayed. Therefore, for example, even in a case in which the film cassette is covered by the patient, it is possible to estimate the position of the film cassette from the film frame. Therefore, JP1994-217973A (JP-H06-217973A) is limited to imaging using an imaging stand, but does not have difficulty in supporting positioning even in a case in which the electronic cassette is covered by the patient.

However, in order to create the film frame, it is necessary to capture the image of the film cassette in the same field of view as that in a case in which radiography is actually performed, using the camera, in a state in which the patient is absent, or it is necessary to acquire the SID. For this reason, it is difficult to apply this technique to a case in which free imaging is performed using the electronic cassette.

That is, in free imaging, in some cases, since the patient is an aged person or a person in an emergency situation and does not freely move, it is difficult to capture the image of the electronic cassette in the same field of view as that in a case in which radiography is actually performed, using the camera, in a state in which the patient is absent. Specifically, in a case in which the electronic cassette is inserted between a person who is in an emergency situation, is unconscious, and lies supine on the ground and the ground and radiography is performed, it is not practical that the person in an emergency situation is moved such that a patient is out of the field of view and then the image of the electronic cassette is captured by the camera. In addition, in free imaging, in some cases, it is difficult to simply know the SID. In this case, it is difficult to create the film frame, that is, it is difficult to know the position of the electronic cassette in the camera image. For this reason, it is difficult to apply the technique disclosed in JP1994-217973A (JP-H06-217973A) to free imaging.

An object of the invention is to provide a radiography system that can relatively position a subject and an electronic cassette, without any trouble, even in a case in which the electronic cassette is covered by the subject in free imaging that is performed using the electronic cassette, without using an imaging stand, and a method for operating the radiography system.

In order to achieve the object, according to an aspect of the invention, there is provided a radiography system comprising: a radiation source that irradiates a subject with radiation; an electronic cassette that detects a radiographic image based on the radiation which has been transmitted through the subject; a camera that is attached to the radiation source and outputs a camera image which is an optical image of at least the subject; a position detection unit that outputs a position signal indicating a position of a part of a peripheral portion of the electronic cassette which is disposed at a position facing the radiation source and operates in a state in which at least some components are disposed at an exposure position included in the camera image and in a field of view of the camera; a calculation unit that calculates an in-image cassette position which is a position of the electronic cassette in the camera image, on the basis of a position of the position detection unit in the camera image and the position signal; a composite image generation unit that generates a composite image of the camera image and an index indicating the in-image cassette position; and a display controller that performs control for displaying the composite image on a display unit.

Preferably, the calculation unit calculates, as the in-image cassette position, positions of four corners of an irradiation surface which is irradiated with the radiation in the electronic cassette. In this case, preferably, the composite image generation unit combines, as the index, a frame that is formed by connecting the positions of the four corners with straight lines.

Preferably, the calculation unit calculates a coordinate transformation matrix for transforming a unit coordinate system which is a coordinate system of the position detection unit into a camera coordinate system which is a coordinate system of the camera from the position of the position detection unit in the camera image, and calculates coordinates of the in-image cassette position represented by the camera coordinate system from the coordinate transformation matrix and coordinates of the positions of the four corners of the irradiation surface represented by the unit coordinate system. In this case, preferably, the calculation unit calculates the coordinate transformation matrix from a direction and size of the position detection unit in the camera image in addition to the position of the position detection unit in the camera image.

Preferably, the calculation unit detects a specific position of a side surface of the electronic cassette in the unit coordinate system from the position signal and calculates the positions of the four corners of the irradiation surface on the basis of the detected specific position.

Preferably, the position detection unit includes an image sensor that outputs, as the position signal, a two-dimensional image of a part of the peripheral portion of the electronic cassette.

Preferably, in a case in which the specific position of the side surface of the electronic cassette is detected to calculate the positions of the four corners of the irradiation surface and the position detection unit includes the image sensor, the calculation unit detects at least three positions as the specific position and calculates a rotation angle of the electronic cassette on the basis of the detected at least three positions.

Preferably, the component disposed at the exposure position is the image sensor. In addition, preferably, the image sensor is any one of an optical camera, a time-of-flight camera, an ultrasound sensor, and a radar sensor.

Preferably, the position detection unit includes an electromagnetic wave generation source that generates an electromagnetic wave and an electromagnetic wave detection sensor that is attached to a predetermined position of the electronic cassette and detects the electromagnetic wave.

Preferably, the component disposed at the exposure position is the electromagnetic wave generation source. In addition, preferably, the electromagnetic wave generation source is a magnetic field generation source or a radio wave generation source, and the electromagnetic wave detection sensor is a magnetic detection sensor or a radio wave detection sensor.

Preferably, the position detection unit comprises a wireless transmission unit that wirelessly transmits the position signal and a battery that supplies power to each unit including the wireless transmission unit, and is wirelessly operated.

Preferably, the radiography system further comprises a unit accommodation unit that detachably accommodates the position detection unit. Preferably, in a case in which the position detection unit is detached from the unit accommodation unit, the position detection unit is operated. In addition, preferably, in a case in which the position detection unit includes the battery, the unit accommodation unit comprises a charging unit that charges the battery.

Preferably, a plurality of types of position detection units which are of the same type and have different types of sensors outputting the position signal are prepared. Preferably, a plurality of position detection units having the same type of sensors outputting the position signal are prepared.

According to another aspect of the invention, there is provided a method for operating a radiography system comprising a radiation source that irradiates a subject with radiation and an electronic cassette that detects a radiographic image based on the radiation transmitted through the subject. The method comprises: a camera image acquisition step of acquiring a camera image which is an optical image of at least the subject from a camera that is attached to the radiation source; a position signal acquisition step of acquiring a position signal indicating a position of a part of a peripheral portion of the electronic cassette which is disposed at a position facing the radiation source from a position detection unit that is operated in a state in which at least some components are disposed at an exposure position included in the camera image and in a field of view of the camera; a calculation step of calculating an in-image cassette position which is a position of the electronic cassette in the camera image, on the basis of a position of the position detection unit in the camera image and the position signal;

a composite image generation step of generating a composite image of the camera image and an index indicating the in-image cassette position; and a display control step of performing control for displaying the composite image on a display unit.

According to the invention, some components of the position detection unit that outputs the position signal indicating the position of a part of the peripheral portion of the electronic cassette which is disposed at a position facing the radiation source are disposed at the exposure position included in the camera image and in the field of view of the camera that is attached to the radiation source and outputs the camera image which is the optical image of at least the subject. The in-image cassette position which is the position of the electronic cassette in the camera image is calculated on the basis of the position of the position detection unit in the camera image and the position signal from the position detection unit. The composite image of the camera image and the index indicating the in-image cassette position is generated and displayed. Therefore, it is possible to provide a radiography system that can relatively position a subject and an electronic cassette, without any trouble, even in a case in which the electronic cassette is covered by the subject in free imaging that is performed using the electronic cassette, without using an imaging stand, and a method for operating the radiography system.

BRIEF DESCRIPTION OF THE DRAWINGS

FIG. 4A illustrates a state in which the position detection unit is accommodated in the unit accommodation unit and does not operate and FIG. 4B illustrates a state in which the position detection unit is detached from the unit accommodation unit and starts to operate.

FIG. 9 is a diagram illustrating an order management list.

FIG. 16A illustrates the rotation angle on a roll axis, FIG. 16B illustrates the rotation angle on a yaw axis, and FIG. 16C illustrates the rotation angle on a pitch axis.

FIG. 17A illustrates the rotation angle on the roll axis, FIG. 17B illustrates the rotation angle on the yaw axis, and FIG. 17C illustrates the rotation angle on the pitch axis.

DESCRIPTION OF THE PREFERRED EMBODIMENTS

First Embodiment

Figure 1:
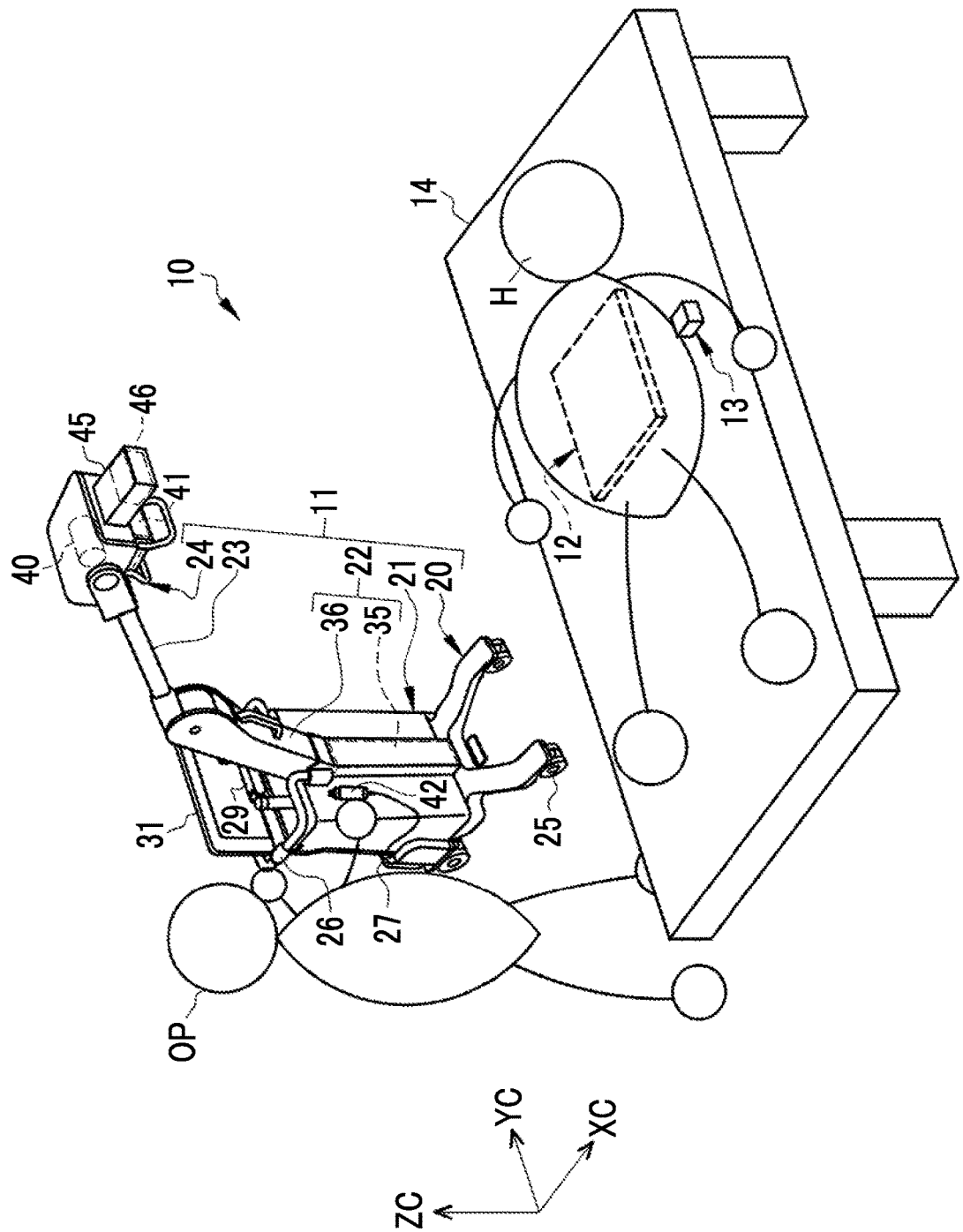
FIG. 1 is a perspective view illustrating an X-ray imaging system.
Figure 2:
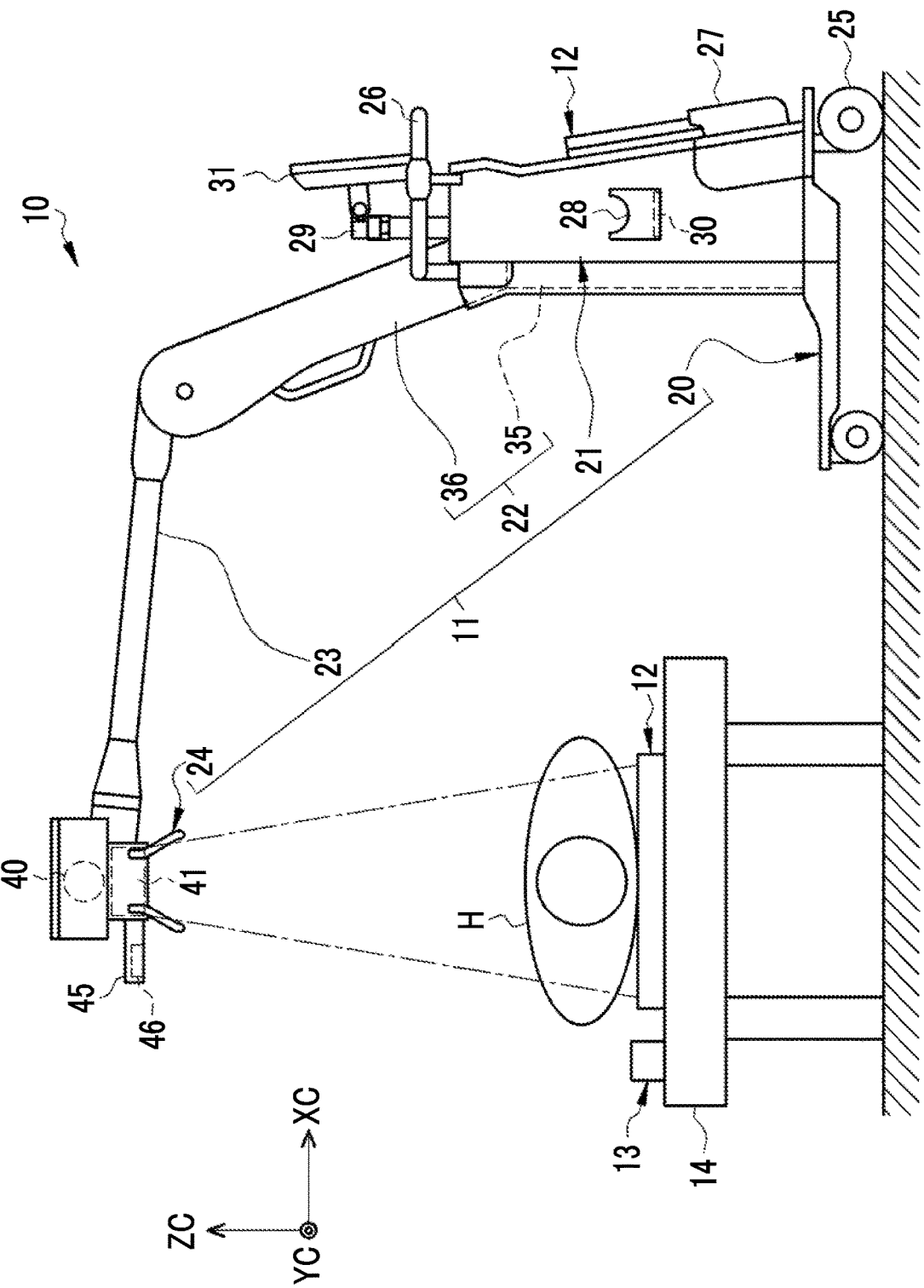
FIG. 2 is a plan view illustrating the X-ray imaging system.

In FIGS. 1 and 2, an X-ray imaging system 10 that uses X-rays as radiation includes, for example, a treatment cart 11, an electronic cassette 12, and a position detection unit 13. An operator OP (not illustrated in FIG. 2) performs free imaging for a subject H that lies on a bed 14 in a hospital room using the X-ray imaging system 10.

The treatment cart 11 is a portable X-ray generation apparatus and includes an axle unit 20, a main body unit 21, a support 22, an arm 23, and an X-ray source 24 corresponding to a radiation source. Four casters 25 are attached to the axle unit 20 and a handle 26 held by the operator OP is attached to the main body unit 21. In a case in which the main body unit 21 is pushed or pulled through the handle 26, the casters 25 are rotated and turned such that the axle unit 20 travels. A locking mechanism (not illustrated) that enables the operator to lock and unlock the rotation and turn of the casters 25 with a one-touch operation is provided in the axle unit 20.

The main body unit 21 is provided with a cassette slot 27, a unit accommodation unit 28 (not illustrated in FIG. 1), and a support arm 29 in addition to the handle 26.

About one to three electronic cassettes 12 are detachably accommodated in the cassette slot 27. The cassette slot 27 includes a charging unit (not illustrated) that charges a battery of the accommodated electronic cassette 12.

The unit accommodation unit 28 is provided on one side surface of the main body unit 21. The position detection unit 13 is detachably accommodated in the unit accommodation unit 28. The unit accommodation unit 28 includes a charging unit 30 that charges a battery 62 (see FIG. 3) of the accommodated position detection unit 13.

A touch panel display (hereinafter, referred to as a touch panel) 31 which is an operation unit and a display unit of a console 55 (see FIG. 3) is attached to the support arm 29. The support arm 29 holds the touch panel 31 so as to be rotatable on a vertical axis, a ZC axis (see FIG. 12) which is an optical axis of a camera 46, and a YC axis perpendicular to the ZC axis in the state illustrated in FIGS. 1 and 2. An XC axis and the YC axis are directions along two sides perpendicular to the field of view (hereinafter, referred to as FOV) of the camera 46 (see FIG. 12).

The support 22 includes a first support 35 and a second support 36. The first support 35 extends upward from the axle unit 20. The first support 35 is buried in the main body unit 21 and is a portion of the main body unit 21 in appearance. The second support 36 is attached to the first support 35 so as to be inclined toward the front side of the treatment cart 11 (in the direction of the subject H). The second support 36 is rotatable on a ZC axis in an angular range of, for example, ±15° with respect to the first support 35.

The base of the arm 23 is attached to the leading end of the second support 36. The arm 23 is rotatable on the YC axis with respect to the second support 36 in the state illustrated in FIGS. 1 and 2. The X-ray source 24 is attached to the leading end of the arm 23 which is a free end. The X-ray source 24 is rotatable on the YC axis with respect to the arm 23 in the state illustrated in FIGS. 1 and 2. Locking mechanisms (not illustrated) that lock rotation are provided in the arm 23 and the X-ray source 24.

The X-ray source 24 includes an X-ray tube 40 that generates X-rays and an irradiation field limiter 41 that limits an irradiation field which is a region irradiated with the X-rays. The X-ray tube 40 includes a filament that emits thermal electrons and a target that collides with the thermal electrons emitted from the filament and emits X-rays. The irradiation field limiter 41 has, for example, a structure in which four lead plates that shield X-rays are provided on each side of a rectangle and a rectangular irradiation opening which transmits X-rays is provided at the center. In this case, the irradiation field limiter 41 moves the positions of the lead plates to change the size of the irradiation opening, thereby setting the irradiation field.

The operator OP sets X-ray irradiation conditions including a tube voltage and a tube current applied to the X-ray tube 40 and the irradiation time of X-rays and the size of the irradiation opening of the irradiation field limiter 41 through the touch panel 31. Here, the tube current is a parameter that determines the flow rate of thermal electrons emitted from the filament of the X-ray tube 40 to a target.

An irradiation switch 42 (not illustrated in FIG. 2) is connected to the main body unit 21. The irradiation switch 42 is operated by the operator OP in a case in which the irradiation of X-rays starts. The irradiation switch 42 is pressed in two stages. In a case in which the irradiation switch 42 is pressed to the first stage (halfway), the X-ray tube 40 starts a preparation operation before generating X-rays. In a case in which the irradiation switch 42 is pressed to the second stage (fully), the X-ray tube 40 generates X-rays. In this way, X-rays are emitted to the subject H.

A camera attachment unit 45 that protrudes toward the front side of the treatment cart 11 is provided on a front surface of the X-ray source 24. The optical camera 46 is provided in the camera attachment unit 45. The camera 46 outputs a camera image 120 (see FIG. 12) which is an optical image of at least the subject H. In this example, the camera image 120 is a color image and is a motion picture.

Since the camera 46 is provided in the camera attachment unit 45 provided in the X-ray source 24, the camera 46 is attached to the X-ray source 24. As such, "a camera attached to a radiation source" described in the claims includes a case in which the camera is directly attached to a peripheral portion of the radiation source and a case in which the camera is provided in the radiation source. In addition, "the camera attached to the radiation source" described in the claims includes a case in which an objective lens is provided in the peripheral portion of the radiation source and an imaging element is provided in a portion (for example, the arm 23) other than the radiation source. Furthermore, the camera 46 may be fixed to the X-ray source 24 so as not to be detachable as in this example or may be detachably provided in the X-ray source 24.

In a case in which the treatment cart 11 is not used, for example, the treatment cart 11 is provided in a preparation room close to an imaging room of a radiology department in a medical facility. During visit imaging in which the operator visits the hospital room in which the subject H is present and takes the image of the subject H, the treatment cart 11 is moved from the preparation room to the hospital room by the operator OP. In a case in which the treatment cart 11 is moved from the preparation room, the operator OP inserts a predetermined electronic cassette 12 used for visit imaging into the cassette slot 27.

The electronic cassette 12 is inserted into a space between the subject H and the bed 14 so as to face the X-ray source 24. Therefore, as represented by a dashed line in FIG. 1, at least a portion of the electronic cassette 12 is covered by the subject H as viewed from the X-ray source 24 (see FIG. 12). The electronic cassette 12 detects an X-ray image 72 (see FIG. 8; corresponding to a radiographic image) based on the X-rays which have been emitted from the X-ray source 24 and then transmitted through the subject H.

The position detection unit 13 is provided on the side of the subject H on the bed 14. The position detection unit 13 outputs a position signal indicating a position that faces the X-ray source 24 and is the position of a part of the peripheral portion of the electronic cassette 12 provided on the back side of the subject H as viewed from the X-ray source 24.

Figure 3:
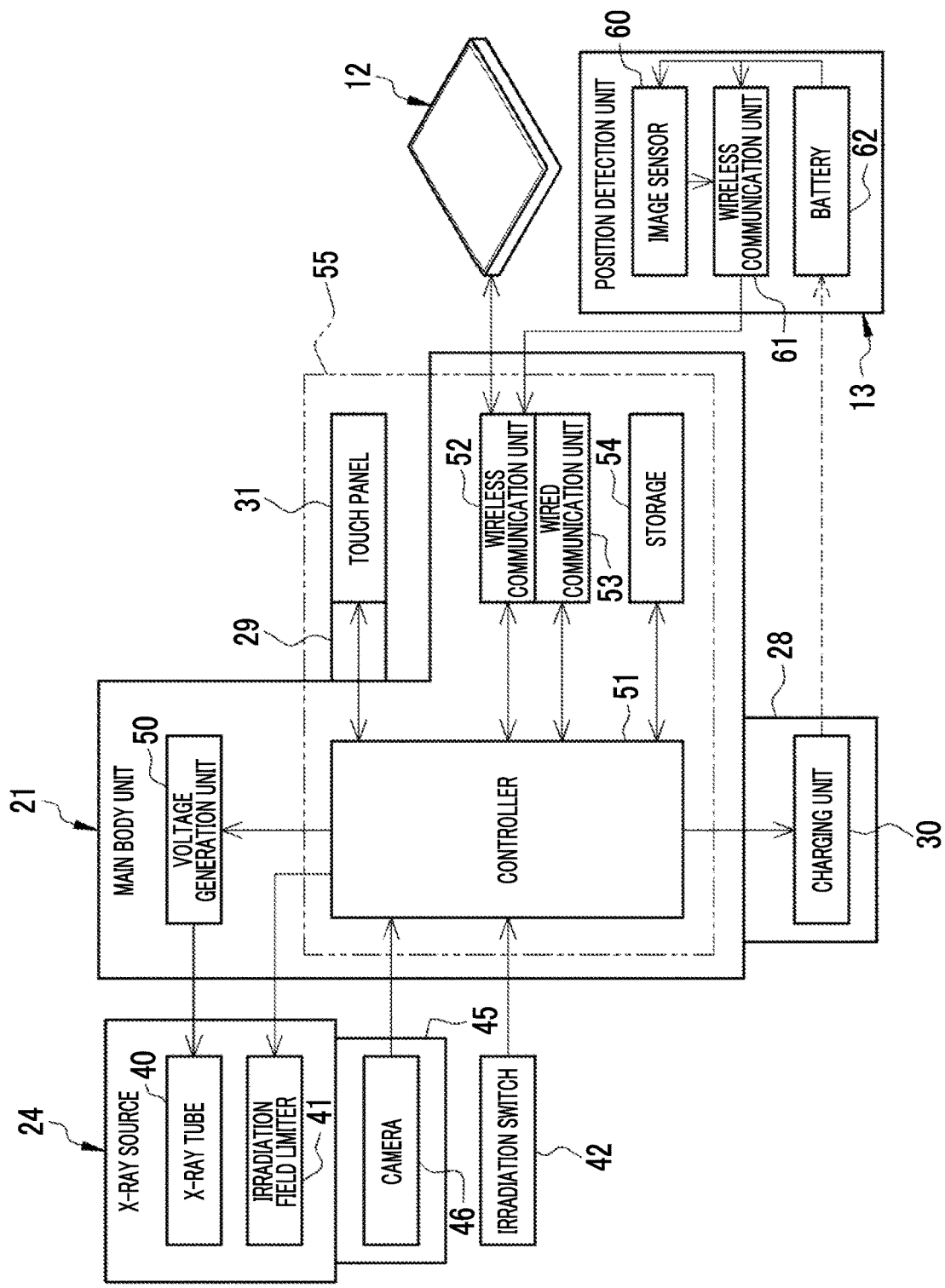
FIG. 3 is a functional block diagram illustrating a treatment cart and a position detection unit.

In FIG. 3, the main body unit 21 is provided with a voltage generation unit 50, a controller 51, a wireless communication unit 52, a wired communication unit 53, and a storage device (hereinafter, referred to as a storage) 54. The voltage generation unit 50 generates a tube voltage to be applied to the X-ray tube 40. The controller 51 controls the operation of the voltage generation unit 50 to control the tube voltage, a tube current, and the irradiation time of X-rays. The controller 51 includes a timer that starts to measure time in a case in which the X-ray tube 40 generates X-rays and stops the operation of the X-ray tube 40 in a case in which the time measured by the timer reaches the irradiation time set in irradiation conditions. The controller 51 operates the irradiation field limiter 41 such that the size of the irradiation opening is equal to the size set through the touch panel 31.

The charging unit 30 and the irradiation switch 42 are connected to the controller 51. The controller 51 controls the operation of the charging unit 30 such that the battery 62 of the position detection unit 13 is charged. In addition, the controller 51 directs the X-ray tube 40 to start a preparation operation in response to an operation of pressing the irradiation switch 42 halfway and directs the X-ray tube 40 to generate X-rays in response to an operation of fully pressing the irradiation switch 42.

The wireless communication unit 52 transmits and receives various kinds of information, such as the X-ray image 72, to and from the electronic cassette 12 using wireless communication. The wired communication unit 53 has the same function as the wireless communication unit 52 except that it performs wired communication.

Examples of the information transmitted from the wireless communication unit 52 or the wired communication unit 53 to the electronic cassette 12 include a preparation operation start signal, an irradiation start signal, and an irradiation end signal. The preparation operation start signal is transmitted in a case in which the preparation operation of the X-ray tube 40 starts in response to the operation of pressing the irradiation switch 42 halfway. The irradiation start signal is transmitted in a case in which the X-ray tube 40 generates X-rays in response to the operation of fully pressing the irradiation switch 42, that is, in a case in which the emission of X-rays starts. The irradiation end signal is transmitted in a case in which the time measured by the timer is equal to the irradiation time set in the irradiation conditions and the operation of the X-ray tube 40 is stopped, that is, in a case in which the emission of X-rays ends.

The wireless communication unit 52 receives the position signal from the position detection unit 13. The wireless communication unit 52 outputs the received position signal to the controller 51. In addition, the wireless communication unit 52 performs wireless communication on the basis of a communication protocol based on the IEEE (The Institute of Electrical and Electronics Engineers, Inc.) 802.11 series. Alternatively, the wireless communication unit 52 performs wireless communication based on a known communication standard, such as proximity infrared communication or Bluetooth (registered trademark) communication.

The storage 54 is, for example, a hard disk drive. The storage 54 stores, for example, a control program, such as an operating system, various application programs, and various kinds of data associated with the programs.

The touch panel 31, the controller 51, the wireless communication unit 52, the wired communication unit 53, and the storage 54 form the console 55. The console 55 includes a work memory that is used by the controller 51 to perform processes, in addition to the above.

The position detection unit 13 includes an image sensor 60, a wireless transmission unit 61, and the battery 62. The image sensor 60 outputs, as the position signal, a two-dimensional image of a part of the peripheral portion of the electronic cassette 12.

The image sensor 60 is any one of an optical camera, a time-of-flight camera 150 (see FIG. 25), an ultrasound sensor, and a radar sensor. The time-of-flight camera 150 irradiates a detection target with a laser beam. The ultrasound sensor irradiates the detection target with ultrasonic waves. The radar sensor irradiates the detection target with radio waves. Then, the camera or the sensor receives waves reflected from the detection target, converts the information of the received reflected waves into a two-dimensional image, and outputs the two-dimensional image. The image sensor 60 forms a so-called stereo camera including two optical cameras, two time-of-flight cameras 150, two ultrasound sensors, or two radar sensors. Therefore, for example, it is possible to obtain information in a ZC-axis direction (depth direction) from a two-dimensional image captured by two optical cameras having parallax.

The wireless transmission unit 61 wirelessly transmits the position signal (in this example, the two-dimensional image) received from the image sensor 60 to the wireless communication unit 52. The wireless communication unit 52 is set as the wireless transmission destination of the position signal in the wireless transmission unit 61 in advance. The wireless transmission unit 61 performs wireless communication based on a known communication standard, similarly to the wireless communication unit 52.

The battery 62 supplies power to the image sensor 60 and the wireless transmission unit 61. The position detection unit 13 is wirelessly operated by the wireless transmission unit 61 and the battery 62. In addition, a wired transmission unit that transmits the position signal to the wired communication unit 53 of the console 55 in a wired manner may be provided in the position detection unit 13.

Figure 4B:
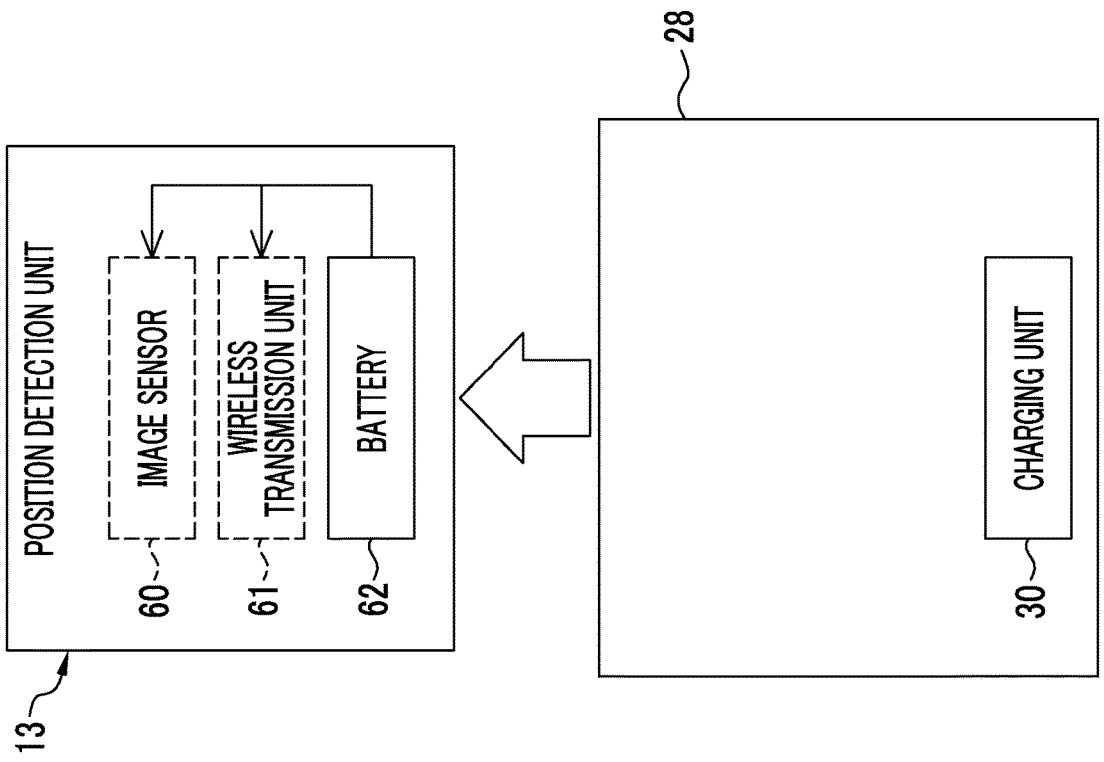
FIGS. 4A and 4B are diagrams illustrating the start-up time of the position detection unit.
Figure 4A:
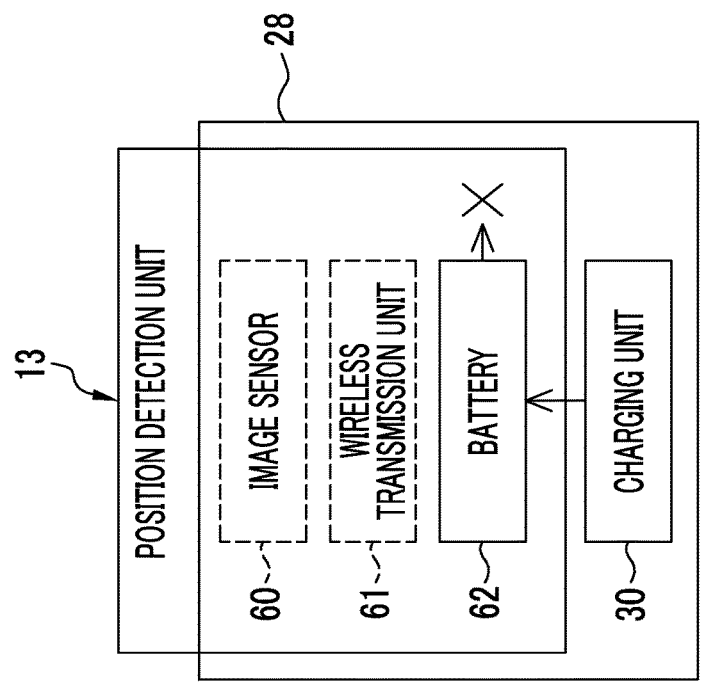

FIG. 4A illustrates an aspect in which the position detection unit 13 is accommodated in the unit accommodation unit 28 and the battery 62 is charged by the charging unit 30. In this case, the battery 62 does not supply power to the image sensor 60 and the wireless transmission unit 61 as represented by X. That is, in a case in which the position detection unit 13 is accommodated in the unit accommodation unit 28, the image sensor 60 and the wireless transmission unit 61 are not operated.

In contrast, in a case in which the position detection unit 13 is detached from the unit accommodation unit 28 as illustrated in FIG. 4B, the supply of power from the battery 62 to the image sensor 60 and the wireless transmission unit 61 starts. That is, in a case in which the position detection unit 13 is detached from the unit accommodation unit 28, the image sensor 60, the wireless transmission unit 61, and the position detection unit 13 are operated.

The main body unit 21 includes a power supply unit (not illustrated) that supplies power to each unit, such as the charging unit 30, the voltage generation unit 50, and the console 55. The power supply unit includes a rechargeable battery. Alternatively, the power supply unit is connected to a commercial power supply and is supplied with power. An independent dedicated power supply unit may be provided in the console 55 in consideration of the stability of various control processes of the controller 51 or the stability of the communication of the wireless communication unit 52 and the wired communication unit 53.

Figure 5:
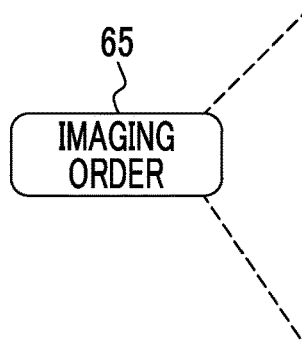
FIG. 5 is a diagram illustrating an imaging order.

The console 55 receives the input of an imaging order 65 illustrated in FIG. 5. The imaging order 65 is, for example, information for commanding the operator OP to perform X-ray imaging which is received from a person who requests imaging, such as a doctor in a diagnosis and treatment department. The imaging order 65 is transmitted from, for example, a radiology information system (RIS; not illustrated) to the console 55.

The imaging order 65 includes items, such as an order ID (identification data), a subject ID, an imaging procedure, and information indicating whether visit imaging is required. The order ID is a symbol or a number for identifying each imaging order 65 and is automatically given by the RIS. The subject ID of the subject H that is an imaging target is described in the subject ID item. The subject ID is a symbol or a number for identifying each subject H.

The imaging procedure is information related to an imaging part of the subject H and the posture and direction of the imaging part. The imaging part is a body part, such as the head, the cervical vertebra, the chest, the abdomen, a hand, a finger, an elbow, or a knee. The posture is the posture of the subject H, such as an upright position, a decubitus position, or a seated position, and the direction is the direction of the subject H with respect to the X-ray source 24, such as the front, the side, or the rear.

Whether the subject H that is an imaging target requires visit imaging is described in the item indicating whether visit imaging is required. The imaging order 65 includes subject information items, such as the name, sex, age, height, and weight of the subject H, in addition the above-mentioned items. In addition, the imaging order 65 includes items, such as a diagnosis and treatment department to which a person who requests imaging belongs, the ID of the person who requests imaging, the date and time when the imaging order 65 is received by the RIS, the purpose of imaging, such as the monitoring of conditions after the surgery or the determination of the effect of treatment remedies, and orders issued from the person who requests imaging to the operator OP.

Figure 6:
FIG. 6 is a diagram illustrating a menu and condition table.

The storage 54 stores a menu and condition table 68 illustrated in FIG. 6. An imaging menu defining an imaging procedure which is a set of the imaging part, the posture, and the direction and irradiation conditions corresponding to the imaging menu are registered in the menu and condition table 68 so as to be associated with each other. Sets of the imaging menu and the irradiation conditions include a set registered as a default, a set obtained by the editing of the default set by the operator OP, and a newly added set other than the default set.

Figure 7:
FIG. 7 is a diagram illustrating a cassette registration table.

In FIG. 7, the storage 54 stores a cassette registration table 70 in which a cassette ID for identifying each electronic cassette 12 and a set of, for example, a name, the size of an imaging region, the size of an outward appearance (a vertical width, a horizontal width, and a thickness), and correction information are registered. For example, a maximum of five electronic cassettes 12 can be registered in the cassette registration table 70.

The name of each electronic cassette 12 given by the operator OP is registered in the name item. The correction information is information unique to each electronic cassette 12 and is the source information of various correction processes performed for the X-ray image 72. Specifically, the correction information is the information of a defective pixel among the pixels of the electronic cassette 12 or the information of offset gain for correcting a variation in the sensitivity of each pixel.

The console 55 displays an imaging order list which is a list of the content of the imaging order 65 illustrated in FIG. 5 on the touch panel 31 in response to an operation of the operator OP. The operator OP sees the imaging order list and checks the content of the imaging order 65. Then, the console 55 displays a selection window having a plurality of electronic cassettes 12 registered in the cassette registration table 70 illustrated in FIG. 7 as alternatives. The operator OP selects an electronic cassette 12 used for X-ray imaging among the plurality of electronic cassettes 12 for each imaging order 65 in the selection window.

Then, the console 55 displays the content of the menu and condition table 68 illustrated in FIG. 6 on the touch panel 31 in a format in which the imaging menu can be set. The operator OP selects and sets an imaging menu matched with the imaging procedure designated by the imaging order 65. The console 55 transmits various kinds of information, such as the imaging menu set by the operator OP, the irradiation conditions corresponding to the set imaging menu, the order ID, and a console ID which is symbol or a number for identifying the console 55, to the electronic cassette 12 through the wireless communication unit 52.

Figure 8:
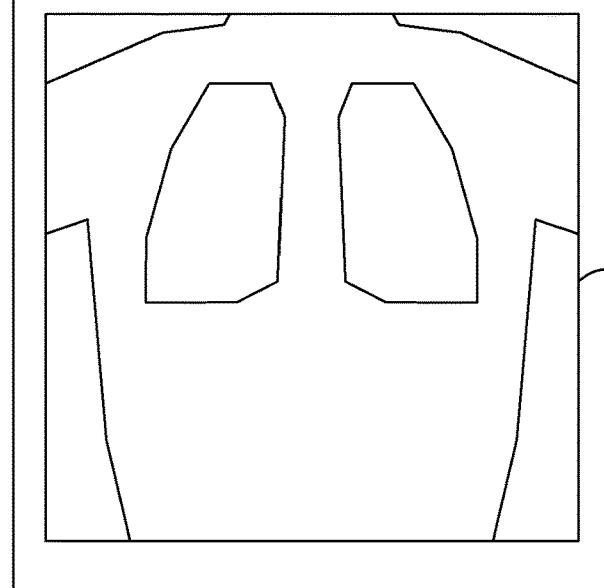
FIG. 8 is a diagram illustrating an image file.

For example, the console 55 converts the X-ray image 72 into an image file 73 in the format based on a Digital Imaging and Communication in Medicine (DICOM) standard illustrated in FIG. 8 and transmits the image file 73 to a picture archiving and communication system (PACS) (not illustrated).

In the image file 73, the X-ray image 72 and accessory information 74 are associated with each other by one image ID. The accessory information 74 includes, for example, subject information, an order ID, an imaging menu, and irradiation conditions. The person who requests imaging can access the PACS with a client terminal, download the image file 73, and see the X-ray image 72 with the client terminal.

The console 55 makes an order management list 78 illustrated in FIG. 9. In the order management list 78, the subject ID of the subject H that is an imaging target, the room number of a hospital room, an imaging completion situation, the cassette ID of the electronic cassette 12 selected to be used for imaging by the operator OP, the imaging menu set by the operator OP, the irradiation conditions corresponding to the set imaging menu, and the image ID of the X-ray image 72 corresponding to the imaging order 65 are registered for the order ID of each imaging order 65.

The image ID of the X-ray image 72 received from the electronic cassette 12 with the cassette ID registered in the cassette ID item is registered in the image ID item. For the period for which the X-ray image 72 is not received from the electronic cassette 12, no image ID is registered in the image ID item and the image ID item is empty. In addition, for example, subject information, the name of the electronic cassette 12, and ID or name of the operator OP who is in charge of imaging are registered in the order management list 78.

In some cases, one imaging order 65 is issued to one subject H or a plurality of imaging orders 65 are issued to one subject H at the same time. In a case in which a plurality of imaging orders 65 are issued to one subject H at the same time, identification codes indicating that the orders are related to one subject H, such as order IDs "OD0001-A" and "OD0001-B" for a subject ID "H0500", are given to the order IDs of the plurality of imaging orders 65.

The electronic cassette 12 transmits the X-ray image 72 to the console 55 together with its own cassette ID and the order ID. The console 55 collates the order ID transmitted together with the X-ray image 72 with the order ID registered in the order management list 78. In addition, the console 55 collates the cassette ID transmitted together with the X-ray image 72 with the cassette ID registered in the order management list 78. The collation makes it possible for the console 55 to recognize which of the order IDs registered in the order management list 78 the received X-ray image 72 corresponds to and to recognize whether the electronic cassette 12 which is the transmission source of the X-ray image is the same as the electronic cassette 12 of the cassette ID registered in the order management list 78.

In a case in which the order ID transmitted together with the X-ray image 72 has been registered in the order management list 78 and the cassette ID transmitted together with the X-ray image 72 is the same as the cassette ID registered in the order management list 78, the console 55 converts the X-ray image 72 into the image file 73 and registers the image ID of the X-ray image 72 in the image ID item of the order management list 78.

Figure 10:
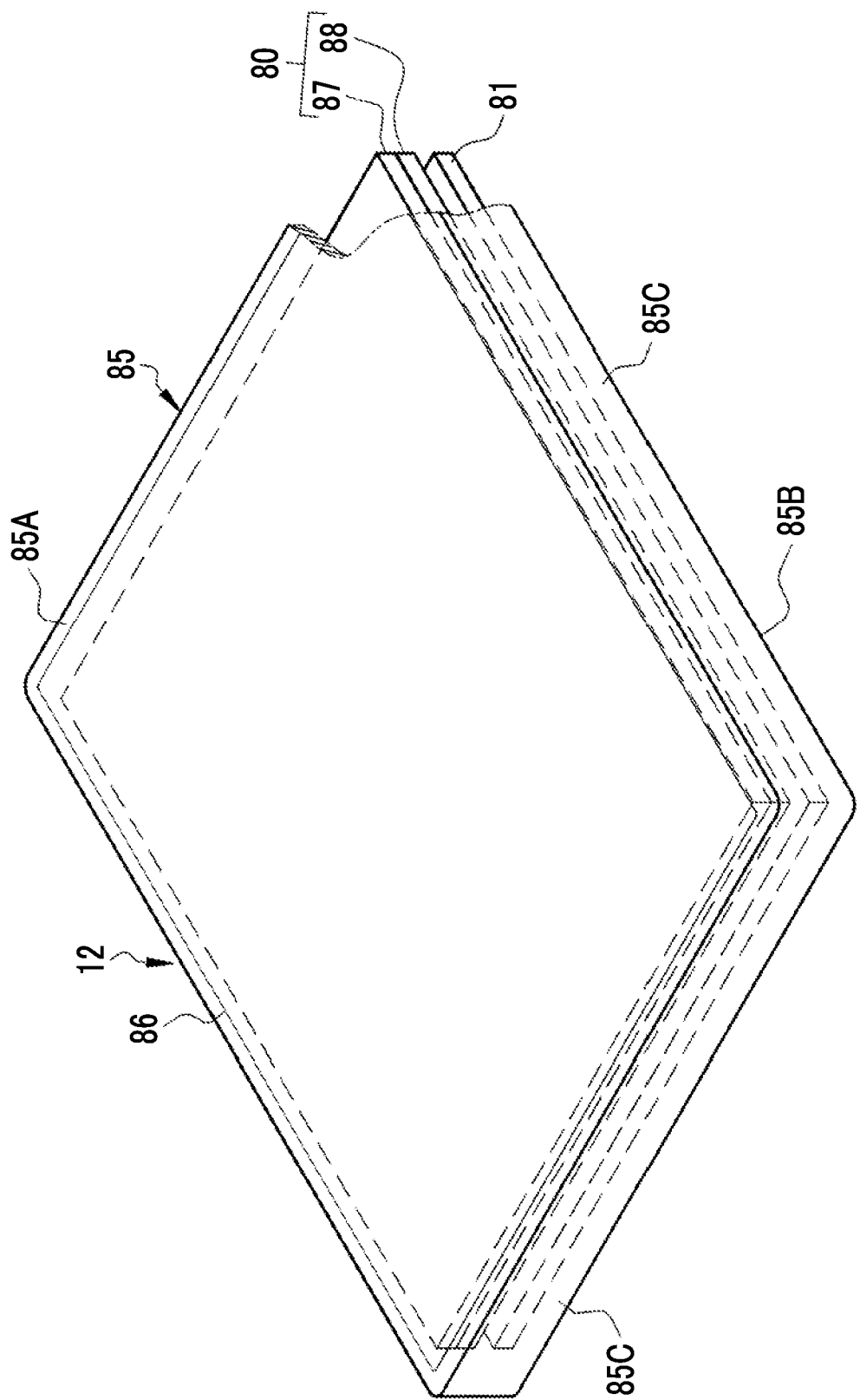
FIG. 10 is a perspective view illustrating the outward appearance of an electronic cassette.

In FIG. 10, the electronic cassette 12 includes a sensor panel 80, a circuit unit 81, and a portable housing 85 having a rectangular parallelepiped shape capable of accommodating the sensor panel 80 and the circuit unit 81. The housing 85 has a front surface 85A, a rear surface 85B that is opposite to the front surface 85A, and four side surfaces 85C that are perpendicular to the front surface 85A and the rear surface 85B. For example, the housing 85 has a size based on International Organization for Standardization (ISO) 4090:2001 which is substantially equal to the size of a film cassette, an imaging plate (IP) cassette, or a computed radiography (CR) cassette.

The front surface 85A, the rear surface 85B, and the side surfaces 85C form a peripheral portion of the electronic cassette 12. Therefore, a part of the peripheral portion of the electronic cassette 12 is a portion of the front surface 85A, the rear surface 85B, and the side surfaces 85C.

A rectangular opening is formed in the front surface 85A and a transmission plate 86 that transmits X-rays is attached to the opening. The electronic cassette 12 is positioned such that the front surface 85A faces the X-ray source 24 and the front surface 85A is irradiated with X-rays. Therefore, the front surface 85A is an irradiation surface. In a case in which an inclined surface obtained by cutting the corners of the front surface 85A and the side surface 85C is formed between the front surface 85A and the side surface 85C, the irradiation surface is a combination of the front surface 85A and the inclined surface. In addition, a wireless communication unit and a battery are provided in the housing 85, which is not illustrated in the drawings. Therefore, the electronic cassette 12 is wirelessly operated. The housing 85 includes a switch for turning on and off a main power supply and an indicator indicating the operation state of the electronic cassette 12 such as the remaining operating time of the battery or the completion state of preparation for imaging.

The sensor panel 80 includes a scintillator 87 and an optical detection substrate 88. The scintillator 87 and the optical detection substrate 88 are stacked in the order of the scintillator 87 and the optical detection substrate 88 as viewed from the front surface 85A. The scintillator 87 has a phosphor, such as CsI:Tl (thallium-activated cesium iodide) or GOS ($Gd_2O_2S$:Tb, terbium-activated gadolinium oxysulfide), converts the X-rays incident through the transmission plate 86 into visible light, and emits the visible light. A sensor panel may be used in which the optical detection substrate 88 and the scintillator 87 are stacked in this order as viewed from the front surface 85A irradiated with the X-rays. In addition, a direct-conversion-type sensor panel may be used which directly converts the X-rays into signal charge using a photoconductive film such as an amorphous selenium film.

The optical detection substrate 88 detects the visible light emitted from the scintillator 87 and converts the visible light into charge. The circuit unit 81 controls the driving of the optical detection substrate 88 and generates the X-ray image 72 on the basis of the charge output from the optical detection substrate 88.

An imaging region is provided in the optical detection substrate 88. The imaging region has a size that is substantially equal to the size of the transmission plate 86 and includes a plurality of pixels which are arranged in a two-dimensional matrix of N rows and M columns. Charge corresponding to the visible light from the scintillator 87 is accumulated in the pixel. The circuit unit 81 converts the charge accumulated in the pixel into a digital signal to detect the X-ray image 72.

Here, N and M are integers that are equal to or greater than 2. For example, N and M are about 2000. In addition, the number of pixels in the matrix is not limited thereto. The array of the pixels may be a square array. Alternatively, the pixels may be inclined at 45° and may be arranged in zigzag.

Figure 11:
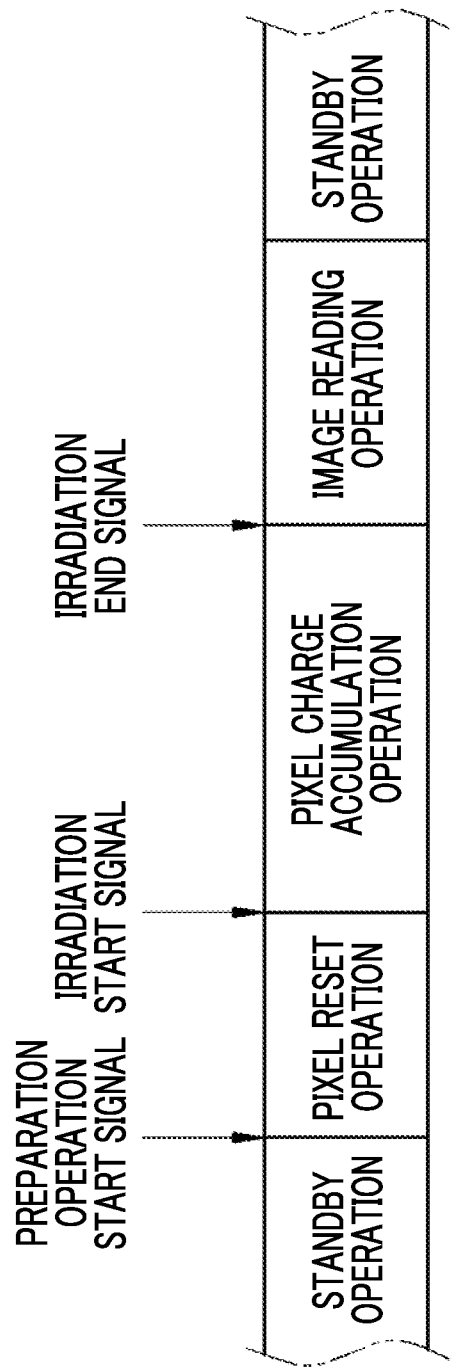
FIG. 11 is a diagram illustrating the flow of an operation of the electronic cassette.

As illustrated in FIG. 11, in a case in which a preparation operation start signal is received from the console 55, the electronic cassette 12 starts a pixel reset operation that reads a dark current from the pixel and resets (discards) the pixel. The electronic cassette 12 performs a standby operation before receiving the preparation operation start signal. The standby operation supplies power to only a minimum number of necessary units such as the wireless communication unit receiving the preparation operation start signal.

Then, in a case in which an irradiation start signal is received from the console 55, the electronic cassette 12 determines that the emission of X-rays has started, ends the pixel reset operation, and starts a pixel charge accumulation operation that accumulates the pixel with the charge corresponding to the amount of X-rays reached. In this way, it is possible to synchronize the time when the X-ray source 24 starts to emit X-rays with the time when the pixel charge accumulation operation starts.

Then, in a case in which an irradiation end signal is received from the console 55, the electronic cassette 12 determines that the emission of X-rays has ended, ends the pixel charge accumulation operation, and starts an image reading operation for reading the X-ray image 72 for diagnosis. In this way, one X-ray imaging operation for obtaining the X-ray image 72 corresponding to a single screen ends. After the image reading operation ends, the electronic cassette 12 returns to the standby operation again.

Figure 12:
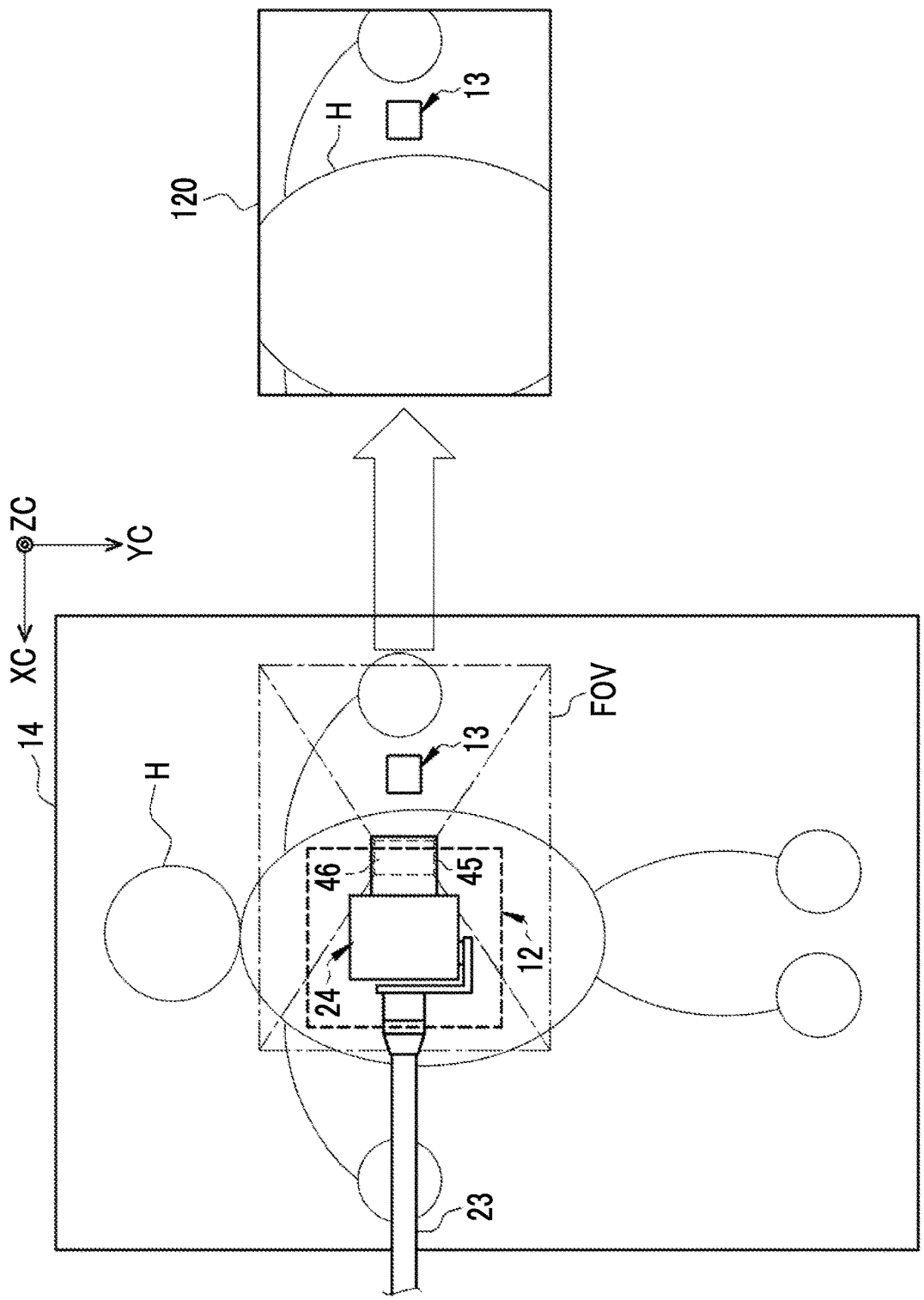
FIG. 12 is a diagram illustrating an aspect of free imaging as viewed from an X-ray source and a camera image.

The left side of an arrow in FIG. 12 is a diagram illustrating an aspect of the free imaging illustrated in FIGS. 1 and 2 as viewed from the X-ray source 24. In this example, the optical axis ZC of the camera 46 is aligned with the vertical axis. In addition, the axes XC and YC of two sides perpendicular to the FOV are aligned with the horizontal axis. In this case, for example, the upper half of the body including the chest which is an imaging part of the subject H, the left arm of the subject H, and the position detection unit 13 which is provided between the upper half of the body and the left arm on the bed 14 are present in the FOV of the camera 46. Therefore, the camera image 120 output from the camera 46 includes the upper half of the body of the subject H, the left arm of the subject H, and the position detection unit 13 as illustrated on the right side of the arrow.

As such, the position detection unit 13 is operated in a state in which at least some components are disposed at an exposure position included in the camera image 120 and in the FOV of the camera 46. In other words, the exposure position is a position that is not covered by the subject H unlike the electronic cassette 12. As illustrated in FIG. 3, the position detection unit 13 includes the image sensor 60. Therefore, in this embodiment, at least some components of the position detection unit 13 disposed at the exposure position are the image sensor 60.

Figure 13:
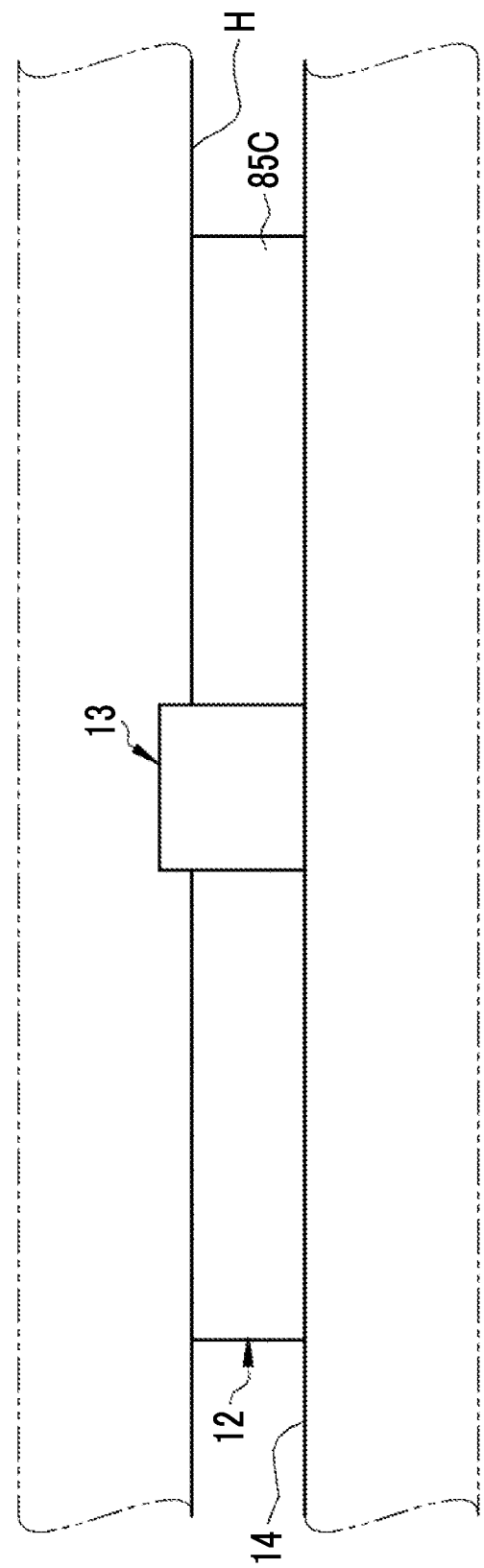
FIG. 13 is a diagram illustrating a side surface of the electronic cassette seen through a gap between a subject and a bed.

In addition, as illustrated in FIG. 13, the position detection unit 13 detects the side surface 85C of the electronic cassette 12 (housing 85) through a gap between the subject H and the bed 14. Therefore, the image sensor 60 of the position detection unit 13 outputs a two-dimensional image of the side surface 85C as a part of the peripheral portion of the electronic cassette 12.

Figure 14:
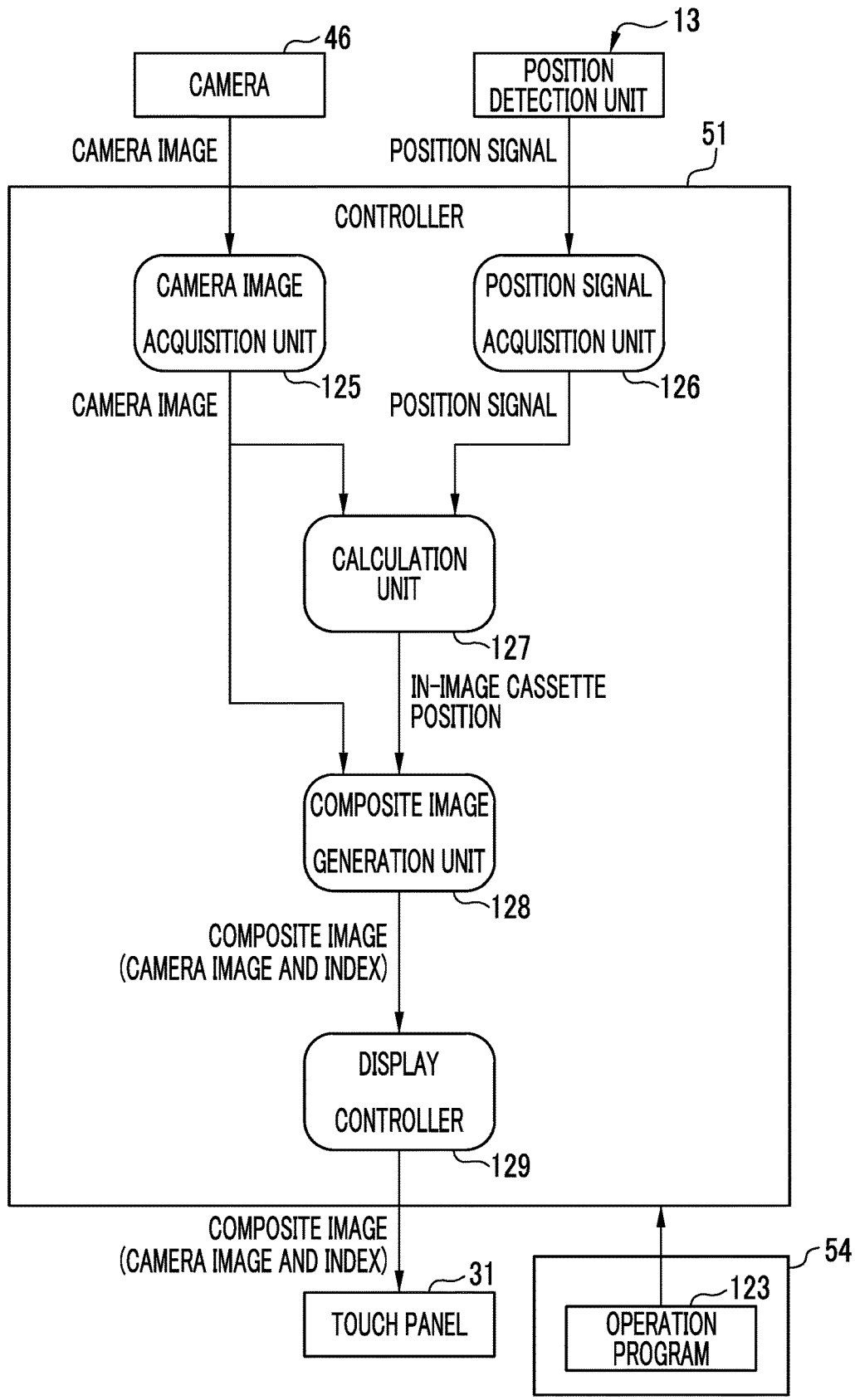
FIG. 14 is a functional block diagram illustrating a controller of a console.

In FIG. 14, the storage 54 stores an operation program 123. In a case in which the operation program 123 is run, the controller 51 of the console 55 functions as a camera image acquisition unit 125, a position signal acquisition unit 126, a calculation unit 127, a composite image generation unit 128, and a display controller 129.

The camera image acquisition unit 125 has a camera image acquisition function of acquiring the camera image 120 from the camera 46. The camera image acquisition unit 125 outputs the acquired camera image 120 to the calculation unit 127 and the composite image generation unit 128. The position signal acquisition unit 126 has a position signal acquisition function of acquiring the position signal from the position detection unit 13. The position signal acquisition unit 126 outputs the acquired position signal to the calculation unit 127.

The calculation unit 127 has a calculation function of calculating an in-image cassette position which is the position of the electronic cassette 12 in the camera image 120. The calculation unit 127 calculates the in-image cassette position on the basis of the position, direction, and size of the position detection unit 13 in the camera image 120 from the camera image acquisition unit 125 and the position signal from the position signal acquisition unit 126. The calculation unit 127 outputs the calculated in-image cassette position to the composite image generation unit 128.

Figure 19:
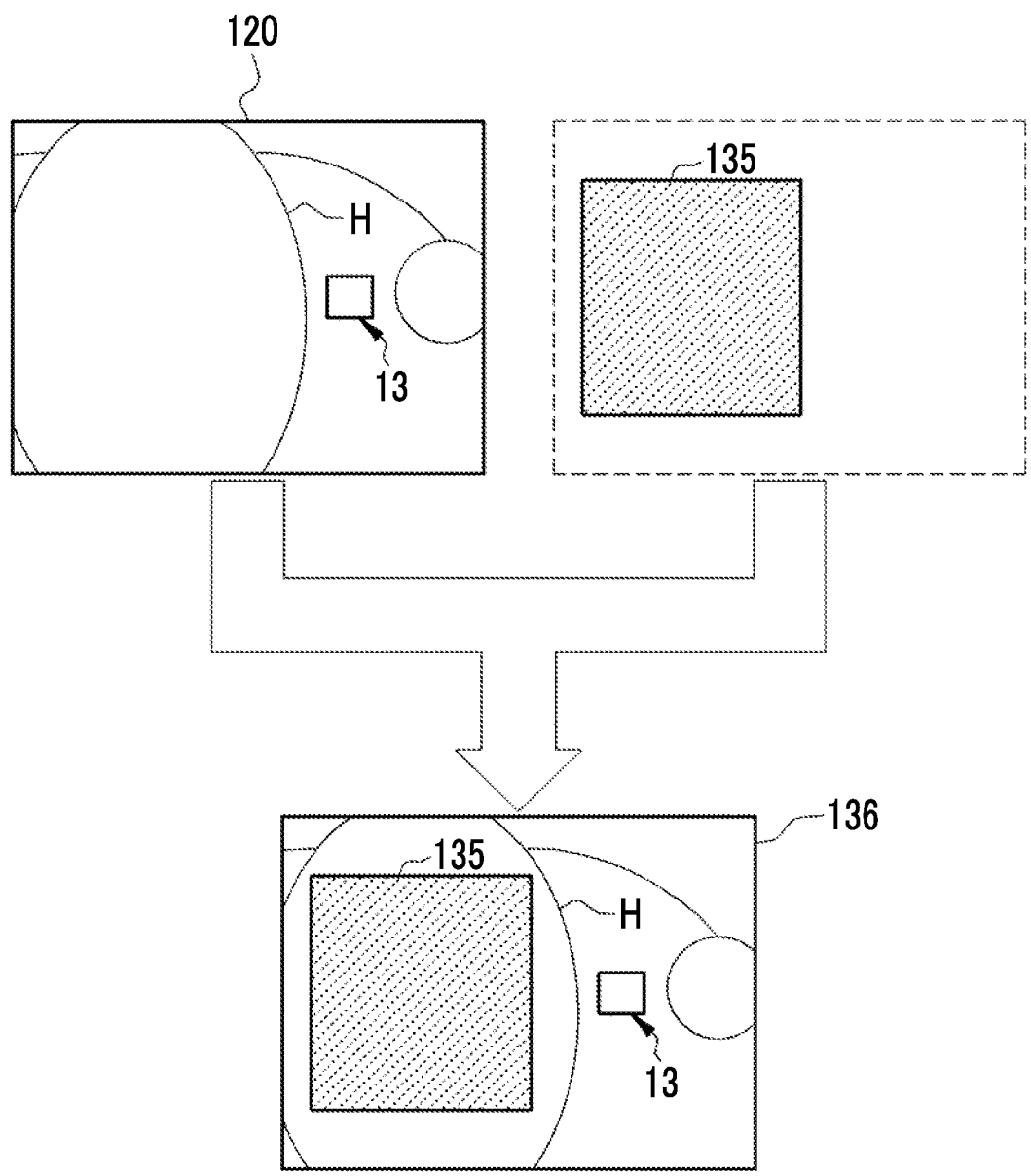
FIG. 19 is a diagram illustrating the generation of a composite image.

The composite image generation unit 128 has a composite image generation function of combining the camera image 120 from the camera image acquisition unit 125 and an index indicating the in-image cassette position from the calculation unit 127 to generate a composite image 136 (see FIG. 19). The composite image generation unit 128 outputs the generated composite image 136 to the display controller 129.

The display controller 129 has a display control function of performing control for displaying the composite image 136 from the composite image generation unit 128 on the touch panel 31 which is a display unit.

The controller 51 also has a function of detecting that the position detection unit 13 has been detached from the unit accommodation unit 28. The units 125 to 129 start to operate in a case in which the detachment of the position detection unit 13 from the unit accommodation unit 28 has been detected and continue their operations until the preparation operation start signal is transmitted to the electronic cassette 12 in response to the operation of pressing the irradiation switch 42 halfway. Then, in a case in which the preparation operation start signal has been transmitted to the electronic cassette 12, the units 125 to 129 stop their operations. That is, the units 125 to 129 operate only for the period from the detection of the detachment of the position detection unit 13 from the unit accommodation unit 28 to the transmission of the preparation operation start signal to the electronic cassette 12. Therefore, the composite image 136 is displayed on the touch panel 31 only for the period.

Figure 15:
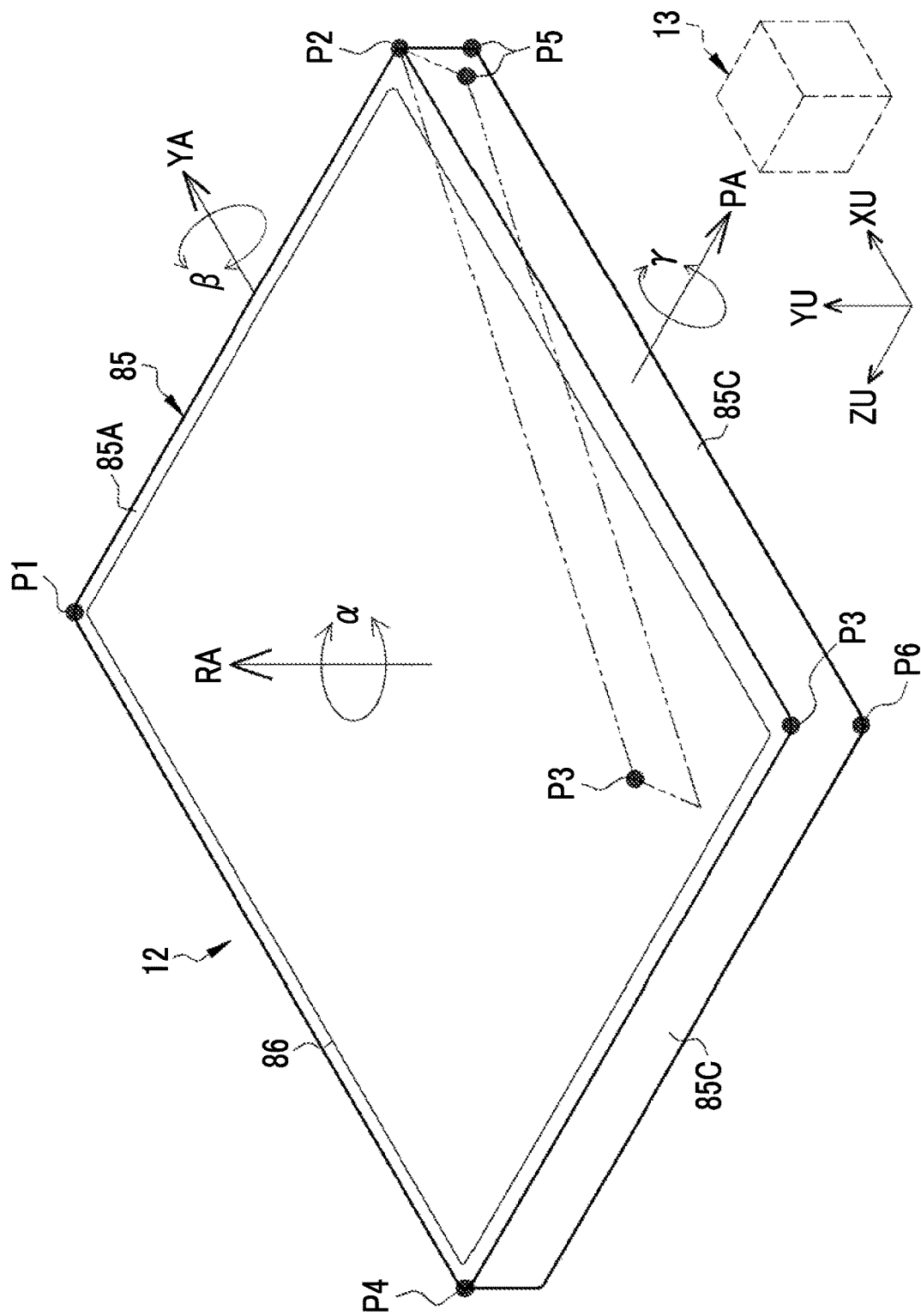
FIG. 15 is a perspective view illustrating the outward appearance of the electronic cassette in which, for example, four corners of an irradiation surface and rotation angles are illustrated.

As illustrated in FIG. 15, the calculation unit 127 calculates, the in-image cassette position, the positions of four corners P1, P2, P3, and P4 of the front surface 85A which is an irradiation surface of the electronic cassette 12. As a stage before this stage, the calculation unit 127 detects a specific position of the side surface 85C of the electronic cassette 12 from the position signal. Specifically, the calculation unit 127 detects at least three positions as the specific position of the side surface 85C. Specifically, the three positions are three corners among the four corners of the side surface 85C. For example, in a case in which the position detection unit 13 is disposed at the position represented by a dashed line, the three positions are two corners P2 and P3 among the four corners P1 to P4 of the front surface 85A and a corner P5 of the rear surface 85B which is opposite to the corner P2. In addition, a corner P6 which is opposite to the corner P3 may be further added as at least three positions.

All of three corners of the side surface 85C are end points of the sides formed by two side surfaces 85C that are perpendicular to each other. Therefore, three corners of the side surface 85C can be detected from the two-dimensional image that is output as the position signal from the image sensor 60 by a known image recognition technique such as edge extraction.

Here, a coordinate system (XU, YU, ZU) drawn in the vicinity of the position detection unit 13 indicates a unit coordinate system which is a coordinate system of the position detection unit 13 with respect to a camera coordinate system (XC, YC, ZC) illustrated in, for example, FIG. 12 which is a coordinate system of the camera 46. A ZU axis is the optical axis of the image sensor 60. An XU axis and a YU axis are directions along two perpendicular sides of the field of view of the image sensor 60. The three positions of the side surface 85C detected from the position signal are represented by the unit coordinate system (XU, YU, ZU).

The two-dimensional image output from the image sensor 60 includes the information of the distance from the image sensor 60 to the three positions of the side surface 85C along the ZU axis and the information of the rotation angles of the three positions of the side surface 85C on the XU axis and the ZU axis with respect to the image sensor 60. The calculation unit 127 calculates the coordinates of the three positions of the side surface 85C in the unit coordinate system (XU, YU, ZU) on the basis of the information of the distance and the information of the angles.

The calculation unit 127 calculates the rotation angles of the electronic cassette 12 on each axis on the basis of the detected three positions. There are three rotation angles $\alpha$, $\beta$, and $\gamma$ illustrated in FIG. 15. The rotation angle $\alpha$ is a rotation angle on a roll axis RA that passes through the center of the housing 85 and is perpendicular to the front surface 85A and the rear surface 85B. The rotation angle $\beta$ is a rotation angle on a yaw axis YA that passes through the center of the housing 85 and is aligned with the direction of the long side of the front surface 85A and the rear surface 85B. The rotation angle $\gamma$ is a rotation angle on a pitch axis PA that passes through the center of the housing 85 and is aligned with the direction of the short side of the front surface 85A and the rear surface 85B.

Figure 16A:
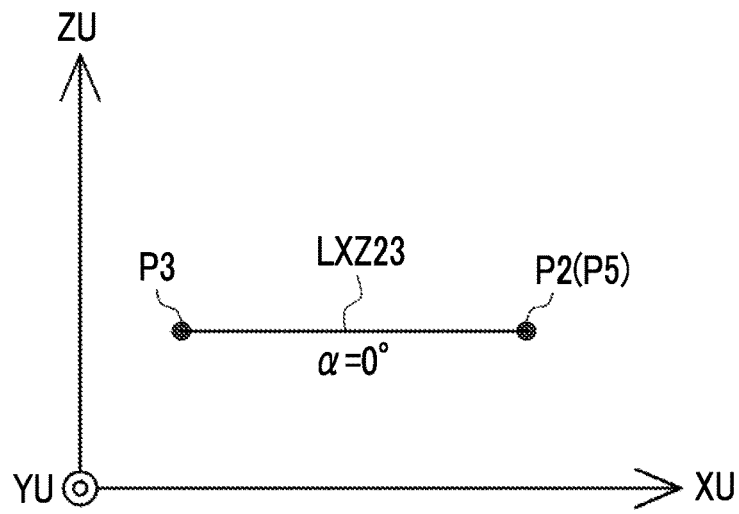
FIGS. 16A to 16C are graphs illustrating the rotation angles of the electronic cassette on each axis in a case in which the electronic cassette is disposed such that each side thereof is parallel to each axis of a unit coordinate system.
Figure 16B:
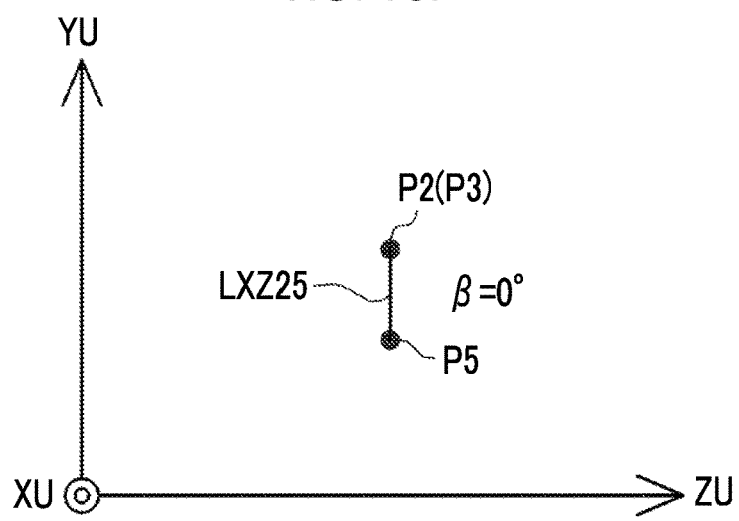
Figure 16C:
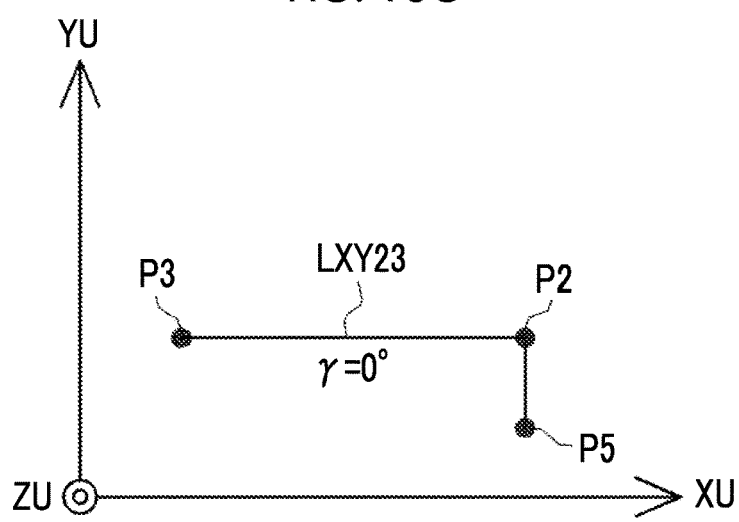

In a case in which the electronic cassette 12 is disposed such that each side thereof is parallel to each axis of the unit coordinate system (XU, YU, ZU) as represented by a solid line in FIG. 15, all of the rotation angles $\alpha$, $\beta$, and $\gamma$ are 0°. That is, the rotation angle $\alpha$ is 0° since a line LXZ23 connecting the corners P2 and P3 which are corners of the long side of the front surface 85A in an XUZU plane is parallel to the XU axis which is the basis of the rotation angle $\alpha$ as illustrated in FIG. 16A. In addition, the rotation angle $\beta$ is 0° since a line LYZ25 connecting the corner P2 and the corner P5 opposite to the corner P2 in a YUZU plane is parallel to the YU axis which is the basis of the rotation angle $\beta$ as illustrated in FIG. 16B. The rotation angle $\gamma$ is 0° since a line LXY23 connecting the corners P2 and P3 in a XUYU plane is parallel to the XU axis which is the basis of the rotation angle $\gamma$ as illustrated in FIG. 16C.

Figure 17A:
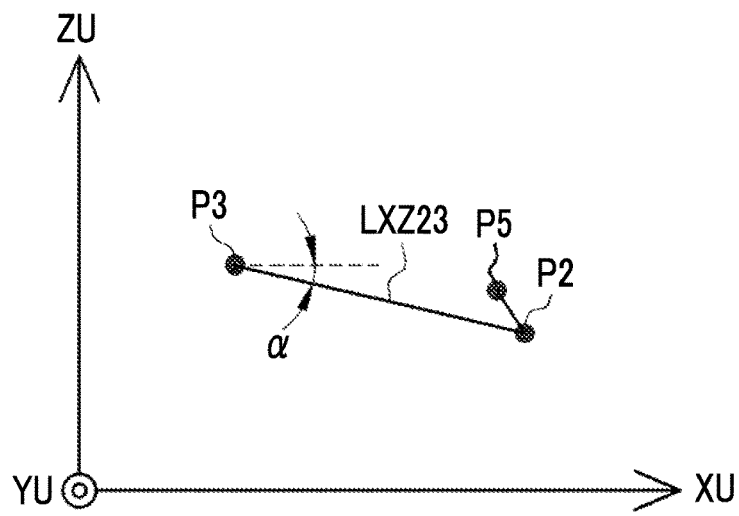
FIGS. 17A to 17C are graphs illustrating the rotation angles of the electronic cassette on each axis in a case in which the electronic cassette is disposed such that each side thereof is inclined with respect to each axis of the unit coordinate system.
Figure 17B:
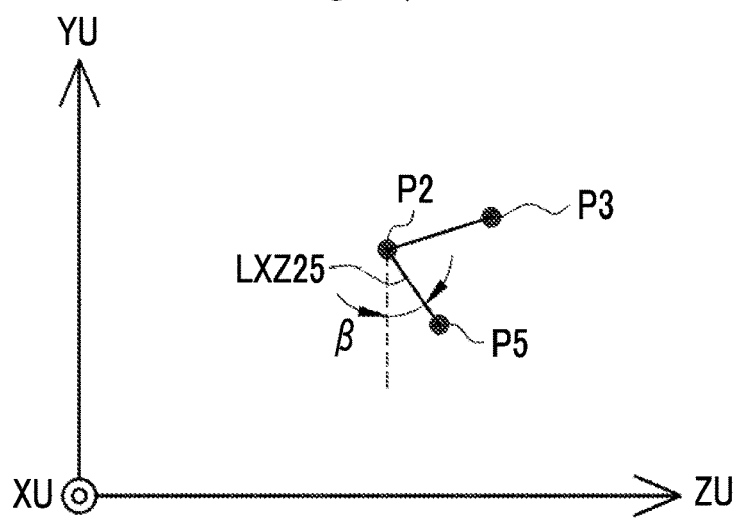
Figure 17C:
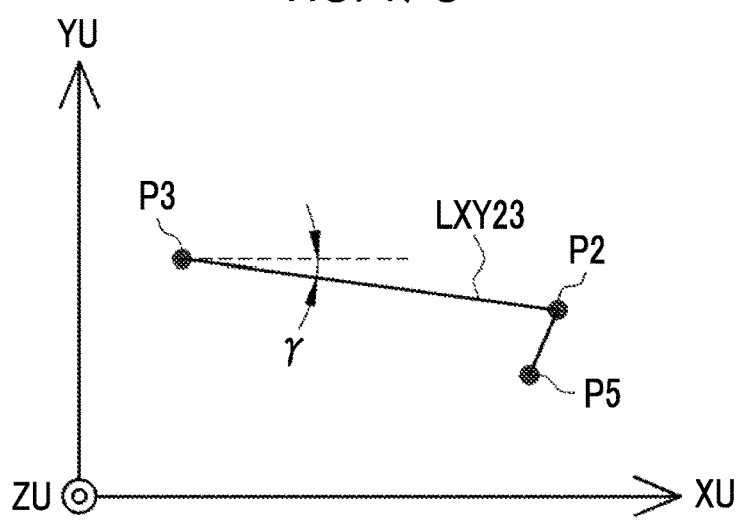

In a case in which the electronic cassette 12 is disposed such that each side thereof is inclined with respect to each axis of the unit coordinate system (XU, YU, ZU) as represented by a two-dot chain line in FIG. 15, the rotation angles $\alpha$, $\beta$, and $\gamma$ are as illustrated in FIGS. 17A to 17C, respectively.

The calculation unit 127 calculates the positions of the corners which have not been calculated among the four corners P1 to P4 of the front surface 85A of the electronic cassette 12 on the basis of the corners whose positions have been calculated among the four corners P1 to P4 of the front surface 85A of the electronic cassette 12, the rotation angles α, β, and γ of the electronic cassette 12, and the known outer size of the electronic cassette 12 registered in the cassette registration table 70. In the case of FIG. 15, the corners whose positions have been calculated are the corners P2 and P3 and the corners whose positions have not been calculated are the corner P1 opposite to the corner P2 and the corner P4 opposite to the corner P3.

Here, the positions of the four corners P1 to P4 of the front surface 85A of the electronic cassette 12 calculated on the basis of the position signal as described above are not represented by the camera coordinate system (XC, YC, ZC), but are represented by the unit coordinate system (XU, YU, ZU). Finally, the positions of the corners P1 to P4 calculated as the in-image cassette position need to be represented by the camera coordinate system (XC, YC, ZC). Therefore, the unit coordinate system (XU, YU, ZU) is transformed into the camera coordinate system (XC, YC, ZC).

In the coordinate system transformation process, the calculation unit 127 calculates a coordinate transformation matrix TM for transforming the unit coordinate system (XU, YU, ZU) into the camera coordinate system (XC, YC, ZC) which is represented by the following Expression (1):

$$(XC, YC, ZC) = TM \times (XU, YU, ZU) \qquad (1).$$

First, the calculation unit 127 recognizes a specific corner or side of the position detection unit 13 in the camera image 120, using a known image recognition technique, and detects the position, direction, and size of the position detection unit 13 in the camera image 120 on the basis of the recognized specific corner or side. Then, the calculation unit 127 calculates the coordinate transformation matrix TM from the detected position, direction, and size of the position detection unit 13. In addition, in a case in which only some components of the position detection unit 13 are disposed at the exposure position, the calculation unit 127 calculates the coordinate transformation matrix TM from the position, direction, and size of some components. The coordinate transformation matrix TM is, for example, a 4×4 matrix and includes a parallel displacement component and a rotational displacement component. Since a known method is used to calculate the coordinate transformation matrix TM, the description thereof will not be repeated.

Figure 18:
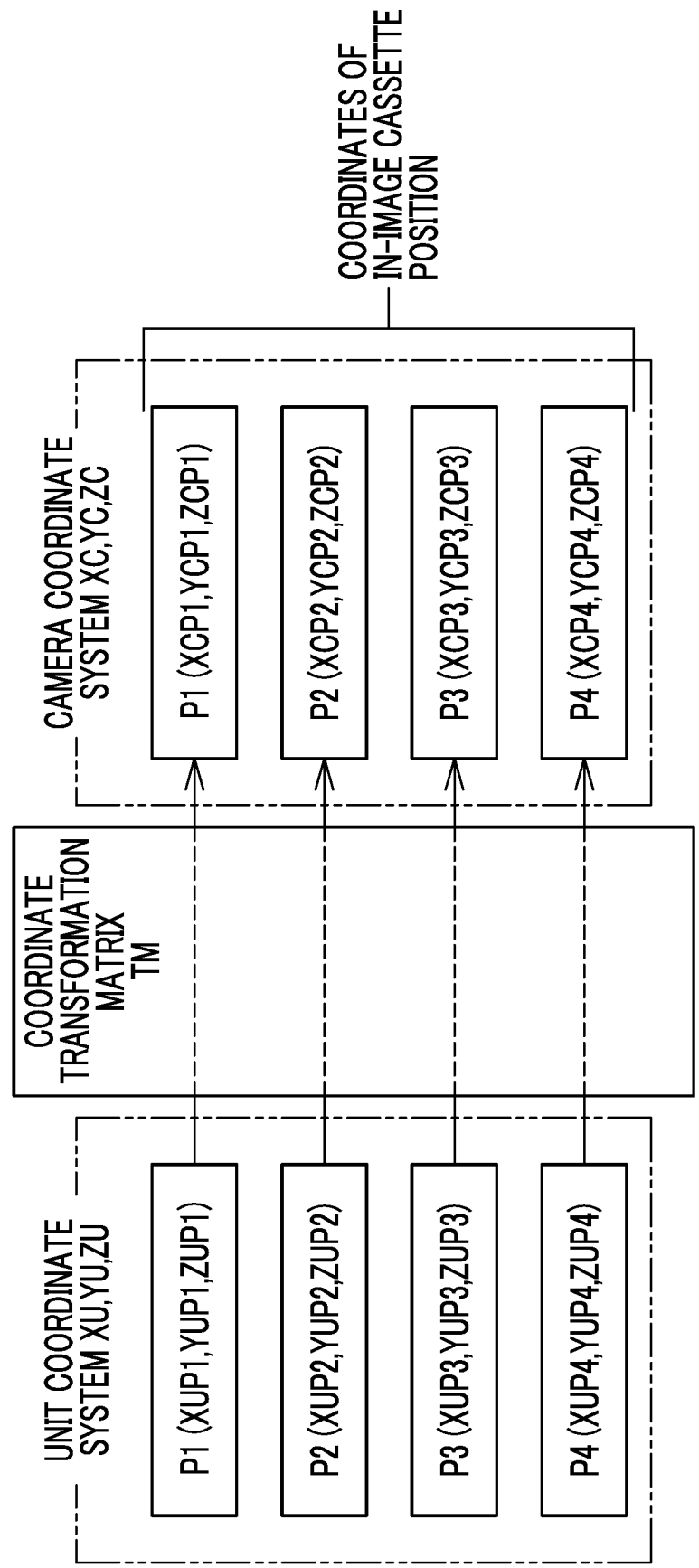
FIG. 18 is a diagram illustrating an aspect in which the coordinates of the positions of four corners represented by the unit coordinate system are transformed into the coordinates represented by a camera coordinate system on the basis of a coordinate transformation matrix.

As illustrated in FIG. 18, the calculation unit 127 calculates the coordinates of the positions of the four corners P1 to P4 represented by the camera coordinate system (XC, YC, ZC) from the coordinate transformation matrix TM and the coordinates of the positions of the four corners P1 to P4 represented by the unit coordinate system (XU, YU, ZU). For example, the calculation unit 127 multiplies the coordinates (XUP1, YUP1, ZUP1) of the position of the corner P1 represented by the unit coordinate system (XU, YU, ZU) by the coordinate transformation matrix TM to calculate the coordinates (XCP1, YCP1, ZCP1) of the position of the corner P1 represented by the camera coordinate system (XC, YC, ZC). The calculation unit 127 outputs the calculated coordinates of the positions of the four corners P1 to P4 represented by the camera coordinate system (XC, YC, ZC) as the coordinates of the in-image cassette position to the composite image generation unit 128.

As illustrated in FIG. 19, the composite image generation unit 128 combines the camera image 120 and a cassette frame 135 which is an index indicating the in-image cassette position to generate the composite image 136. The cassette frame 135 is obtained by connecting four corners of the front surface 85A of the electronic cassette 12 with straight lines and has a rectangular shape corresponding to the outer shape of the front surface 85A. Then, the inside of the rectangular cassette frame 135 is colored in a specific color, for example, green, as hatched.

Next, the operation of the above-mentioned configuration will be described with reference to flowcharts illustrated in FIGS. 20 and 21. First, the operator OP checks the imaging order 65 indicating whether visit imaging is required on the touch panel 31. The operator OP performs the selection of an electronic cassette 12 used for imaging and the setting of an imaging menu for the imaging order 65 indicating whether visit imaging is required, using the touch panel 31. Then, the operator OP loads the electronic cassette 12 used for imaging on the treatment cart 11 and moves the treatment cart 11 to the hospital room in which the subject H is present.

After arriving in the hospital room, the operator OP sees the content of the order management list 78 on the touch panel 31 and checks the subject H, the electronic cassette 12 to be used, and the imaging menu. Then, the operator OP starts to relatively position the X-ray source 24, the electronic cassette 12, and the subject H.

The operator OP detaches the position detection unit 13 from the unit accommodation unit 28 and places the position detection unit 13 at the exposure position. As illustrated in FIG. 4B, the position detection unit 13 starts to operate in a case in which the position detection unit 13 is detached from the unit accommodation unit 28. Therefore, the time and effort of the operator OP turning on the position detection unit 13 are reduced.

In a case in which the position detection unit 13 is detached from the unit accommodation unit 28, the camera image acquisition unit 125, the position signal acquisition unit 126, the calculation unit 127, the composite image generation unit 128, and the display controller 129 start to operate in the controller 51 of the console 55, as illustrated in FIG. 14.

For example, in the case of chest radiography, the operator OP sets the X-ray source 24 immediately above the subject H, using the axle unit 20 or the arm 23, as illustrated in FIG. 1. Then, the operator OP inserts the electronic cassette 12 between the subject H and the bed 14.

The positioning state by the operator OP is captured by the camera 46. In addition, the position detection unit 13 detects three positions of the side surface 85C of the electronic cassette 12 inserted between the subject H and the bed 14.

Figure 20:
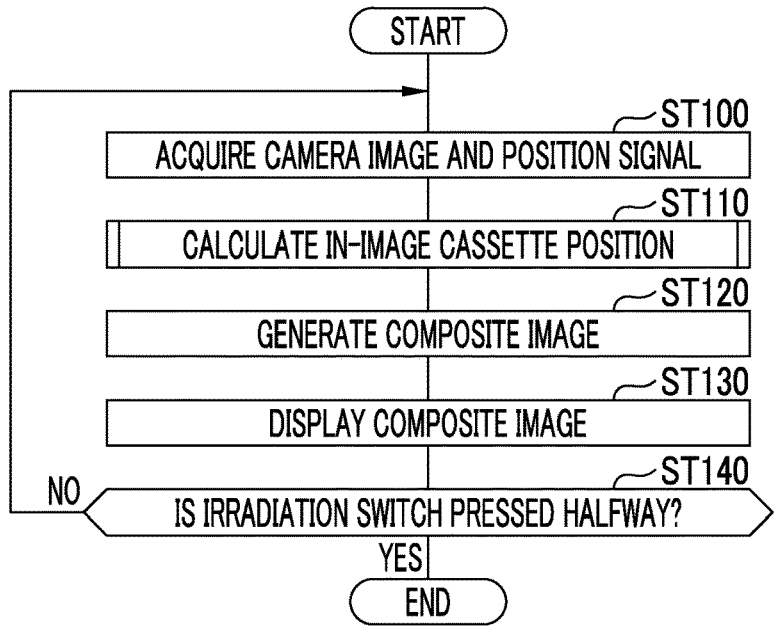
FIG. 20 is a flowchart illustrating the procedure of a process of the controller of the console.

As illustrated in Step ST100 of FIG. 20, camera image acquisition unit 125 acquires the camera image 120 captured by the camera 46 (camera image acquisition step). In addition, the position signal acquisition unit 126 acquires the position signal output from the position detection unit 13 (position signal acquisition step). The camera image 120 is output from the camera image acquisition unit 125 to the calculation unit 127 and the composite image generation unit 128. The position signal is output from the position signal acquisition unit 126 to the calculation unit 127.

The calculation unit 127 calculates the in-image cassette position on the basis of the position, direction, and size of the position detection unit 13 in the camera image 120 from the camera image acquisition unit 125 and the position signal from the position signal acquisition unit 126 (Step ST110; a calculation step).

Figure 21:
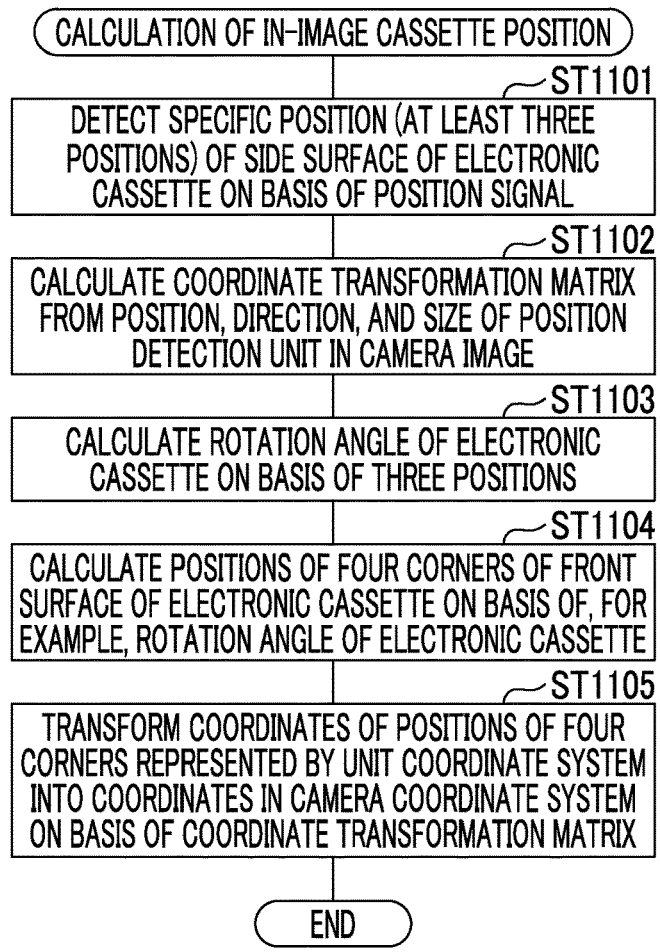
FIG. 21 is a flowchart illustrating the procedure of a process of a calculation unit.

FIG. 21 illustrates a sequence of the calculation step performed by the calculation unit 127. First, at least three positions which are specific positions of the side surface 85C of the electronic cassette 12 are detected on the basis of the position signal (Step ST1101). In parallel to this step, the coordinate transformation matrix TM for transforming the unit coordinate system (XU, YU, ZU) into the camera coordinate system (XC, YC, ZC) from the position, direction, and size of the position detection unit 13 in the camera image 120 (Step ST1102).

After three positions of the side surface 85C of the electronic cassette 12 are detected, the rotation angles $\alpha$, $\beta$, and $\gamma$ of the electronic cassette 12 are calculated on the basis of the detected three positions, as illustrated in FIGS. 16 and 17 (Step ST1103). Then, the positions of the four corners P1 to P4 of the front surface 85A of the electronic cassette 12 are calculated on the basis of, for example, the rotation angles $\alpha$, $\beta$, and $\gamma$ of the electronic cassette 12 or the known outer size of the electronic cassette 12 (Step ST1104).

As illustrated in FIG. 18, the coordinates of the positions of four corners represented by the unit coordinate system (XU, YU, ZU) are transformed into the coordinates of the positions of four corners represented by the camera coordinate system (XC, YC, ZC) on the basis of the coordinate transformation matrix TM calculated in Step ST1102 (Step ST1105). The calculated coordinates of the positions of the four corners P1 to P4 represented by the camera coordinate system (XC, YC, ZC) are output as the coordinates of the in-image cassette position from the calculation unit 127 to the composite image generation unit 128.

In Step ST120 of FIG. 20, the composite image generation unit 128 combines the camera image 120 from the camera image acquisition unit 125 and the cassette frame 135 to generate the composite image 136, as illustrated in FIG. 19 (composite image generation step). The display controller 129 displays the composite image 136 on the touch panel 31 (Step ST130; a display control step). The operator OP performs positioning while seeing the composite image 136 displayed on the touch panel 31.

After positioning, the operator OP operates the irradiation switch 42 to generate X-rays from the X-ray source 24. The series of processes in Steps ST100 to ST130 of FIG. 20 is continuously performed until the irradiation switch 42 is pressed halfway to transmit the preparation operation start signal to the electronic cassette 12 (YES in Step ST140).

The front surface 85A of the electronic cassette 12 is irradiated with the X-rays which have been emitted from the X-ray source 24 and then transmitted through the subject H. In the electronic cassette 12, as illustrated in FIG. 11, the pixel charge accumulation operation and the image reading operation are performed to detect the X-ray image 72. The X-ray image 72 is transmitted from the electronic cassette 12 to the console 55. The X-ray image 72 is converted into the image file 73 by the console 55, is transmitted to the PACS, and is seen by the person who requests imaging.

The operator OP can see the cassette frame 135 of the composite image 136 to reliably recognize the position of the electronic cassette 12 covered by the subject H. Therefore, the operator OP can easily adjust the position of the electronic cassette 12 with respect to the subject H or the position of the X-ray source 24 with respect to the electronic cassette 12. As a result, even in a case in which the electronic cassette 12 is covered by the subject H in free imaging, it is possible to relatively position the subject H and the electronic cassette 12 without any trouble. In a case in which the subject H and the electronic cassette 12 are relatively positioned without any, an imaging mistake that a desired imaging part is not included in the X-ray image 72 does not occur and an unnecessary operation of performing imaging again is prevented.

The operation of the operator OP required to generate the composite image 136 is only the operation of detaching the position detection unit 13 from the unit accommodation unit 28 and placing the position detection unit 13 at the exposure position. The position detection unit 13 starts to operate in operative association with the action of detaching the unit accommodation unit 28. Therefore, it is possible to generate the composite image 136 useful for the relative positioning between the subject H and the electronic cassette 12, without increasing the workload of the operator OP.

The calculation unit 127 calculates the positions of the four corners P1 to P4 of the front surface 85A as the in-image cassette position. Therefore, it is easy to generate the cassette frame 135 which is an index indicating the in-image cassette position.

The calculation unit 127 calculates the coordinate transformation matrix TM from the position, direction, and size of the position detection unit 13 in the camera image 120 and transforms the coordinates of the positions of the four corners P1 to P4 represented by the unit coordinate system (XU, YU, ZU) into the coordinates represented by the camera coordinate system (XC, YC, ZC) using the coordinate transformation matrix TM. Therefore, it is possible to obtain the coordinates of the in-image cassette position with relatively simple calculation such as matrix calculation.

The coordinate transformation matrix TM may be calculated from only the position of the position detection unit 13 in the camera image 120. However, it is preferable to calculate the coordinate transformation matrix TM from the direction and size of the position detection unit 13 in the camera image 120, in addition to the position of the position detection unit 13 in the camera image 120, in order to increase the accuracy of the coordinate transformation matrix TM.

The calculation unit 127 detects a specific position (at least three positions) of the side surface 85C of the electronic cassette 12 in the unit coordinate system (XU, YU, ZU) from the position signal and calculates the positions of the four corners P1 to P4 on the basis of the detected specific position. Therefore, it is possible to reliably calculate the positions of the four corners P1 to P4 from the specific position of the side surface 85C which can only be detected in a case in which the electronic cassette 12 is covered by the subject H.

The calculation unit 127 detects three positions of the side surface 85C of the electronic cassette 12 and calculates the rotation angles $\alpha$, $\beta$, and $\gamma$ of the electronic cassette 12 on the basis of the detected three positions. Therefore, it is possible to accurately calculate the positions of the four corners P1 to P4, also considering the direction of the electronic cassette 12 with respect to the position detection unit 13.

In a case in which an optical camera is used as the image sensor 60, a marker whose image can be recognized may be attached to a part of the peripheral portion of the electronic cassette 12, for example, the side surface 85C and the position of the marker (the corners of the marker) may be detected as the specific position of the side surface 85C, instead of the positions of the corners of the side surface 85C. The marker has, for example, a rectangular shape and the calculation unit 127 detects at least three corners of the marker as the specific position. In a case in which the distances from the position of the marker to the positions of the corners of the side surface 85C are measured in advance, it is possible to calculate the positions of the corners of the side surface 85C from the position of the marker and to further calculate the positions of the four corners P1 to P4 of the front surface 85A of the electronic cassette 12.

In a case in which only one marker is provided and is covered by the clothes of the subject H or the sheet of the bed 14, it is difficult to detect the specific position. In order to solve the problem, it is preferable that a plurality of markers are attached to the side surface 85C.

The position detection unit 13 includes the wireless transmission unit 61 and the battery 62 and is wirelessly operated. Therefore, it is easy to handle the position detection unit 13, as compared to a case in which the position detection unit is connected to the console 55 by a cable and communicates with the console 55 in a wired manner, and the workload of the operator OP does not increase.

Since the unit accommodation unit 28 in which the position detection unit 13 is detachably accommodated is provided, the operator OP does not need to carry the position detection unit 13.

The unit accommodation unit 28 includes the charging unit 30 that charges the battery 62 of the position detection unit 13. Therefore, it is possible to minimize a situation in which the position detection unit 13 is not available due to a reduction in the capacity of the battery 62.

In the first embodiment, the treatment cart 11 is provided with the unit accommodation unit 28. However, the unit accommodation unit 28 may be provided in the electronic cassette 12, instead of or in addition to the treatment cart 11.

In the first embodiment, the operation of the position detection unit 13 starts in a case in which the position detection unit 13 is detached from the unit accommodation unit 28. However, the invention is not limited thereto. For example, the controller 51 may have a function of determining whether the position detection unit 13 is included in the camera image 120. Then, in a case in which the controller 51 determines that the position detection unit 13 is included in the camera image 120, the controller 51 may transmit a start signal from the wireless communication unit 52 to the position detection unit 13 to start the operation of the position detection unit 13. In this case, the position detection unit 13 includes a wireless communication unit that has both a wireless transmission function and a wireless receiving function, instead of the wireless transmission unit 61. Power is supplied from the battery 62 to the wireless communication unit of the position detection unit 13 before the operation of the position detection unit 13 starts such that the wireless communication unit waits for the reception of the start signal from the wireless communication unit 52 of the console 55.

Alternatively, in a case in which the operator OP sets an imaging menu through the touch panel 31, the start signal may be transmitted from the wireless communication unit 52 to the position detection unit 13 to start the operation of the position detection unit 13. In this case, similarly to the case in which it is determined whether the position detection unit 13 is included in the camera image 120, the position detection unit 13 includes a wireless communication unit with a wireless receiving function and the wireless communication unit waits for the reception of the start signal before the operation of the position detection unit 13 starts.

In addition, in a case in which the position detection unit 13 is detached from the unit accommodation unit 28, the operation of the position detection unit 13 may start. In a case in which the controller 51 determines that the position detection unit 13 is included in the camera image 120, the units 125 to 129 illustrated in FIG. 14 may be constructed in the controller 51. Then, the units 125 to 129 may be operated.

The camera 46 may start to operate at any time or may start to operate at a predetermined time like the position detection unit 13. For example, in a case in which the position detection unit 13 is detached from the unit accommodation unit 28, both the position detection unit 13 and the camera 46 start to operate.

In the first embodiment, the position detection unit 13 is disposed at a position that faces the side surface 85C corresponding to the long side of the electronic cassette 12 and the calculation unit 127 detects the corners P1, P2, and P5 of the side surface 85C corresponding to the long side. However, the position detection unit 13 may be disposed at a position that faces the side surface 85C corresponding to the short side of the electronic cassette 12 and the calculation unit 127 may detect the corners of the long side surface 85C corresponding to the short side.

In addition, a posture sensor may be provided in the electronic cassette 12 and the rotation angles $\alpha$, $\beta$, and $\gamma$ of the electronic cassette 12 may be calculated on the basis of the output of the posture sensor. In this case, for example, only two corners P2 and P3 of the front surface 85A may be detected as the specific position of the side surface 85C of the electronic cassette 12 and it is not necessary to detect the corner P5 of the rear surface 85B.

A marker whose image can be recognized may be attached to the position detection unit 13 in order for the calculation unit 127 to easily detect the position, direction, and size of the position detection unit 13 in the camera image 120.

Second Embodiment

Figure 22:
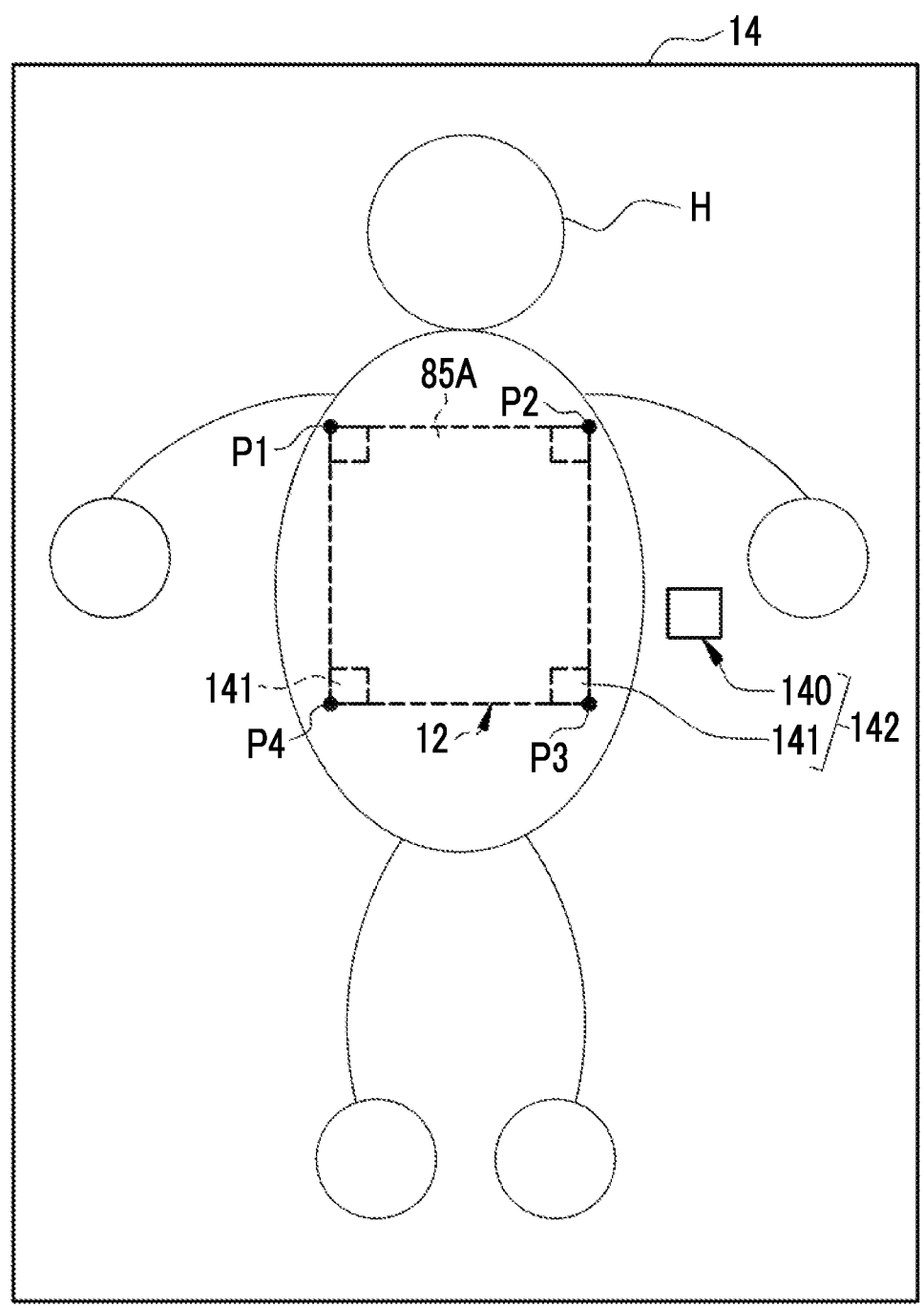
FIG. 22 is a diagram illustrating an aspect of free imaging using a position detection unit including an electromagnetic wave generation source and an electromagnetic wave detection sensor according to a second embodiment.
Figure 23:
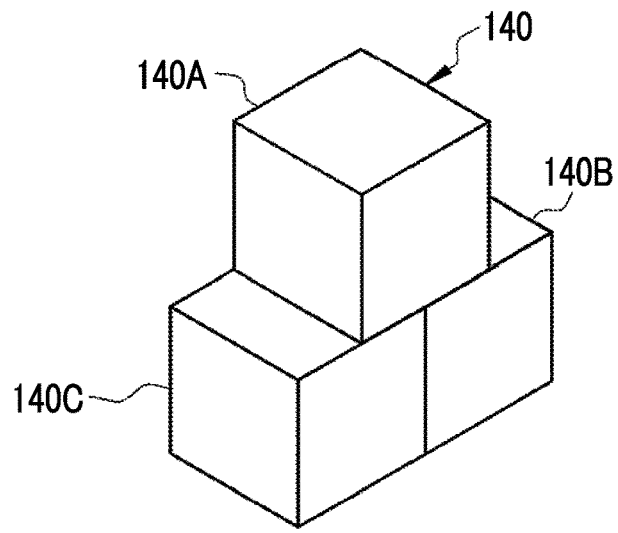
FIG. 23 is a diagram schematically illustrating the electromagnetic wave generation source.

In a second embodiment illustrated in FIGS. 22 and 23, a position detection unit 142 including an electromagnetic wave generation source 140 that generates electromagnetic waves and an electromagnetic wave detection sensor 141 that detects the electromagnetic waves is used instead of the image sensor 60.

In FIG. 22, the electromagnetic wave generation source 140 is disposed at an exposure position. That is, in this embodiment, the electromagnetic wave generation source 140 corresponds to at least some components of the position detection unit disposed at the exposure position. The electromagnetic wave detection sensors 141 are attached to the positions of the four corners P1 to P4 of the front surface 85A which are predetermined positions of the electronic cassette 12. The electromagnetic wave detection sensors 141 may be attached to the corners P1 to P4 so as to be detachable or may be fixed to the corners P1 to P4 so as not to be detachable. In addition, the electromagnetic wave detection sensors 141 may not be attached to the peripheral portion of the electronic cassette 12, but may be provided in the electronic cassette 12.

As illustrated in FIG. 23 which is a diagram schematically illustrating the electromagnetic wave generation source 140, the electromagnetic wave generation source 140 is formed by integrating three electromagnetic wave generation sources 140A, 140B, and 140C. The electromagnetic wave generation sources 140A to 140C have the same size and are arranged at positions corresponding to the vertices of an equilateral triangle.

The electromagnetic wave generation sources 140A to 140C generate electromagnetic waves at different times. Each electromagnetic wave detection sensor 141 detects the electromagnetic waves from the electromagnetic wave generation sources 140A to 140C. Each electromagnetic wave detection sensor 141 wirelessly transmits an intensity signal indicating the intensity of the detected electromagnetic waves to the electromagnetic wave generation sources 140A to 140C.

Since the electromagnetic waves are attenuated depending on the distance, the electromagnetic wave generation sources 140A to 140C calculate the distances to each electromagnetic wave detection sensor 141 on the basis of the intensity signals from each electromagnetic wave detection sensor 141. The electromagnetic wave generation sources 140A to 140C transmit the distances to each electromagnetic wave detection sensor 141 as the position signal to the console 55.

The calculation unit 127 calculates the position of each electromagnetic wave detection sensor 141, that is, the positions of the four corners P1 to P4 of the front surface 85A in the unit coordinate system (XU, YU, ZU) from the known positional relationship between the electromagnetic wave generation sources 140A to 140C and the distance to each electromagnetic wave detection sensor 141 transmitted as the position signal, using a known triangulation principle.

The position detection unit 142 can directly calculate the positions of the four corners P1 to P4 of the front surface 85A as the in-image cassette position from the position signal. Therefore, unlike the first embodiment, it is not necessary to detect a specific position (at least three positions) of the side surface 85C of the electronic cassette 12 and to calculate the rotation angles α, β, and γ of the electronic cassette 12. As a result, it is possible to simply calculate the positions of the four corners P1 to P4 of the front surface 85A and to reduce the processing load of the calculation unit 127. In addition, since unnecessary calculation causing an error is not performed, it is possible to improve the accuracy of calculating the positions of the four corners P1 to P4 of the front surface 85A.

The intensity of the electromagnetic waves is attenuated within a certain range of the electromagnetic wave generation source 140. In a case in which there is an obstacle, the electromagnetic waves are transmitted through the obstacle. Therefore, even in a case in which the side surface 85C of the electronic cassette 12 between the subject H and the bed 14 is hidden by, for example, the clothes of the subject H or the sheet of the bed 14, the position detection unit 142 can output the position signal required to calculate the positions of the four corners P1 to P4 of the front surface 85A. The use situation of the position detection unit 142 is less restricted than that of the position detection unit 13 according to the first embodiment which is not capable of detecting the positions of the four corners P1 to P4 of the front surface 85A in a case in which the side surface 85C of the electronic cassette 12 between the subject H and the bed 14 is not seen.

It is preferable that the electromagnetic wave generation source 140 is a magnetic field generation source or a radio wave generation source. In a case in which the electromagnetic wave generation source 140 is the magnetic field generation source, the electromagnetic wave detection sensor 141 is a magnetic detection sensor. In a case in which the electromagnetic wave generation source 140 is the radio wave generation source, the electromagnetic wave detection sensor 141 is a radio wave detection sensor.

In this embodiment, similarly to the above-described embodiment, it is preferable that the position detection unit 142 is wirelessly operated. Specifically, the electromagnetic wave generation source 140 is provided with a wireless transmission unit that wirelessly transmits the position signal and a battery that supplies power to each unit including the wireless transmission unit. In addition, the electromagnetic wave detection sensor 141 is provided with a wireless transmission unit that wirelessly transmits the intensity signal and a battery that supplies power to each unit including the wireless transmission unit.

A unit accommodation unit that accommodates the position detection unit 142 may be provided. In a case in which the electromagnetic wave detection sensors 141 are attached so as to be detachable from the corners P1 to P4, the unit accommodation unit accommodates both the electromagnetic wave generation source 140 and the electromagnetic wave detection sensors 141. In contrast, in a case in which the electromagnetic wave detection sensors 141 are fixed to the corners P1 to P4, the unit accommodation unit accommodates only the electromagnetic wave generation source 140. A charging unit that charges the battery may also be provided in the unit accommodation unit.

In a case in which the position detection unit 142 is detached from the unit accommodation unit, the operation of the position detection unit 142 may start. In a case in which both the electromagnetic wave generation source 140 and the electromagnetic wave detection sensors 141 are accommodated in the unit accommodation unit, both the electromagnetic wave generation source 140 and the electromagnetic wave detection sensors 141 start to operate when the electromagnetic wave generation source 140 and the electromagnetic wave detection sensors 141 are detached from the unit accommodation unit. In contrast, in a case in which the electromagnetic wave detection sensors 141 are fixed to the corners P1 to P4 and only the electromagnetic wave generation source 140 is accommodated in the unit accommodation unit, the electromagnetic wave generation source 140 starts to operate when it is detached from the unit accommodation unit and transmits a start signal to the electromagnetic wave detection sensors 141. In a case in which the start signal is received from the electromagnetic wave generation source 140, the electromagnetic wave detection sensor 141 starts to operate. The start signal may not be transmitted from the electromagnetic wave generation source 140 to the electromagnetic wave detection sensor 141, but may be transmitted from the console 55 to the electromagnetic wave detection sensor 141. Alternatively, in a case in which the electromagnetic wave detection sensors 141 are fixed to the corners P1 to P4, the electromagnetic wave detection sensors 141 may start to operate in operative association with the start of the operation of the electronic cassette 12.

The position where the electromagnetic wave generation source 140 is disposed may not be the exposure position on the bed 14 illustrated in FIG. 22. The exposure position may be any position where the electromagnetic wave detection sensor 141 can detects the electromagnetic waves. As described above, since the electromagnetic waves are attenuated depending on the distance, it is preferable that the electromagnetic wave generation source 140 is disposed as close to the electromagnetic wave detection sensor 141, that is, the electronic cassette 12 as possible in order to enable the electromagnetic wave detection sensor 141 to detect the electromagnetic waves with relatively low intensity.

The electromagnetic wave generation source 140 may be carried by the operator OP in a state in which it is included in the field of view of the camera 46 as far as possible. In this case, the position of the electromagnetic wave generation source 140 varies depending on the movement of the operator OP. Therefore, the coordinate transformation matrix TM is calculated whenever the operator OP moves. In addition, in this case, the time stamp of the camera image 120 and the position signal is acquired and the calculation of the in-image cassette position by the calculation unit 127 is synchronized with a change in the position of the electromagnetic wave generation source 140 on the basis of the time stamp.

The positions where the electromagnetic wave detection sensors 141 are attached are not limited to the corners P1 to P4 illustrated in FIG. 22. For example, the electromagnetic wave detection sensors 141 may be attached to three corners among the four corners P1 to P4 and the position of the corner to which the electromagnetic wave detection sensor 141 is not attached may be calculated on the basis of the positions of the three corners. Alternatively, the electromagnetic wave detection sensors 141 may be attached to the centers of four sides forming the front surface 85A.

The three electromagnetic wave generation sources 140A, 140B, and 140C may not be prepared and the following configuration may be used: one electromagnetic wave generation source that can change the directionality of electromagnetic waves is used to sequentially emit electromagnetic waves in three different directions and the calculation unit 127 calculates the positions of the four corners P1 to P4 of the front surface 85A on the basis of the position signal obtained by the electromagnetic waves.

Third Embodiment

Figure 24:
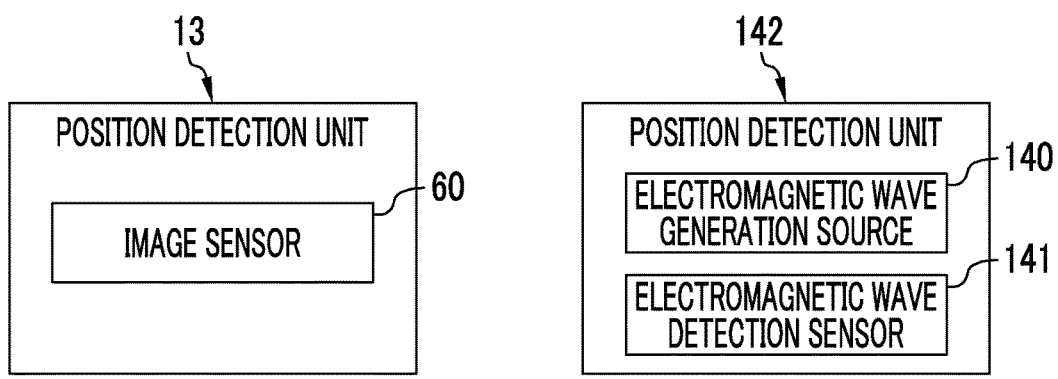
FIG. 24 is a diagram illustrating a third embodiment in which a plurality of types of position detection units having different types of sensors outputting position signals are prepared.

In a third embodiment illustrated in FIG. 24, a plurality of types of position detection units having different types of sensors that output position signals are prepared.

In FIG. 24, in this embodiment, the position detection unit 13 including the image sensor 60 according to the first embodiment and the position detection unit 142 including the electromagnetic wave generation source 140 and the electromagnetic wave detection sensor 141 according to the second embodiment are prepared. In this case, the operator OP normally uses the position detection unit 13 having relatively low power consumption. In contrast, in a special situation, such as a case in which the operator OP wants to increase the accuracy of calculating the in-image cassette position or a case in which the side surface 85C of the electronic cassette 12 between the subject H and the bed 14 is hidden by, for example, the clothes of the subject H or the sheet of the bed 14, the operator OP selects the position detection unit 142. Alternatively, for example, in a case in which the position detection unit 13 is used and the capacity of the battery 62 is reduced, the position detection unit 13 is switched to the position detection unit 142.

As such, in a case in which a plurality of types of position detection units having different types of sensors that output the position signals are prepared, the operator OP can appropriately select a position detection unit corresponding to the situation and use the selected position detection unit.

The plurality of types of position detection units may not be selectively used, but may be disposed at different exposure positions and then operated at the same time. In this case, the calculation unit 127 calculates each in-image cassette position on the basis of different position signals from each position detection unit. In the example illustrated in FIG. 24, the calculation unit 127 calculates the in-image cassette position based on the position signal from the position detection unit 13 and the in-image cassette position based on the position signal from the position detection unit 142.

Then, the calculation unit 127 performs an appropriate weighting process for each in-image cassette position and finally calculates one in-image cassette position to be displayed as the cassette frame 135. For example, the weighting process is performed such that a weight for the in-image cassette position based on the position signal from the position detection unit 142 having relatively high calculation accuracy is high and a weight for the in-image cassette position based on the position signal from the position detection unit 13 is low.

A plurality of types of position detection units having different types of sensors are not limited to the pair illustrated in FIG. 24. For example, a pair of a position detection unit using an optical camera as the image sensor 60 and a position detection unit using the time-of-flight camera 150 as the image sensor 60 may be used. Alternatively, a pair of a position detection unit that uses a magnetic field generation source as the electromagnetic wave generation source 140 and uses a magnetic detection sensor as the electromagnetic wave detection sensor 141 and a position detection unit that uses a radio wave generation source, as the electromagnetic wave generation source 140 and uses a radio wave detection sensor as the electromagnetic wave detection sensor 141 may be used.

In addition, two or more types of position detection units having different types of sensors may be prepared.

A plurality of types of position detection units may be separately provided as illustrated in FIG. 24 or may be integrated with each other. In a case in which a pair of the position detection unit 13 and the position detection unit 142 illustrated in FIG. 24 are integrated with each other, the image sensor 60 and the electromagnetic wave generation source 140 corresponding to some components disposed at the exposure position are integrated with each other.

Fourth Embodiment

Figure 25:
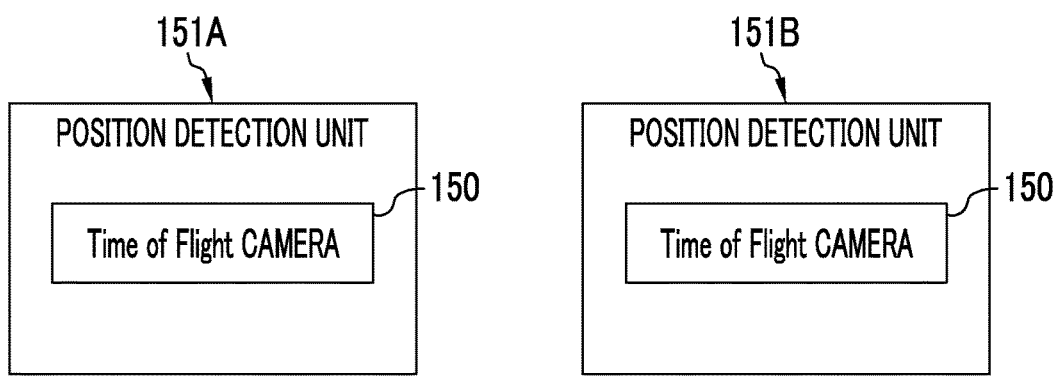
FIG. 25 is a diagram illustrating a fourth embodiment in which a plurality of position detection units that are the same type and have the same type of sensors outputting position signals are prepared.

In a fourth embodiment illustrated in FIG. 25, a plurality of position detection units which are the same type and have the same type of sensors outputting position signals are prepared.

In FIG. 25, in this embodiment, two position detection units 151A and 151B, each of which has the time-of-flight camera 150 as the image sensor, are prepared. In a case in which a plurality of position detection units that are the same type and have the same type of sensors outputting the position signals are prepared, it is possible to respond to various situations on a case-by-case basis, similarly to the third embodiment in which a plurality of types of position detection units having different types of sensors that output the position signals.

In this case, similarly to the third embodiment, a plurality of position detection units of the same type are arranged at different exposure positions and are operated at the same time. Then, the calculation unit 127 may calculate each in-image cassette position on the basis of the position signals from each position detection unit. In this case, a plurality of cassette frames 135 indicating each in-image cassette position may be combined with the camera image 120 such that the operator OP selects the most reliable cassette frame 135. In this case, the time and effort required to move the position detection unit from the exposure position where the in-image cassette position is not calculable to the exposure position where the in-image cassette position is calculable are reduced.

Two or more position detection units which are the same type and have the same type of sensors outputting the position signals may be prepared.

The display unit that displays the composite image 136 is not limited to the touch panel 31 described in each of the above-mentioned embodiments. For example, the composite image 136 may be transmitted from the display controller 129 of the console 55 to a notebook personal computer or a tablet terminal carried by the operator OP and then displayed thereon.

Figure 26:
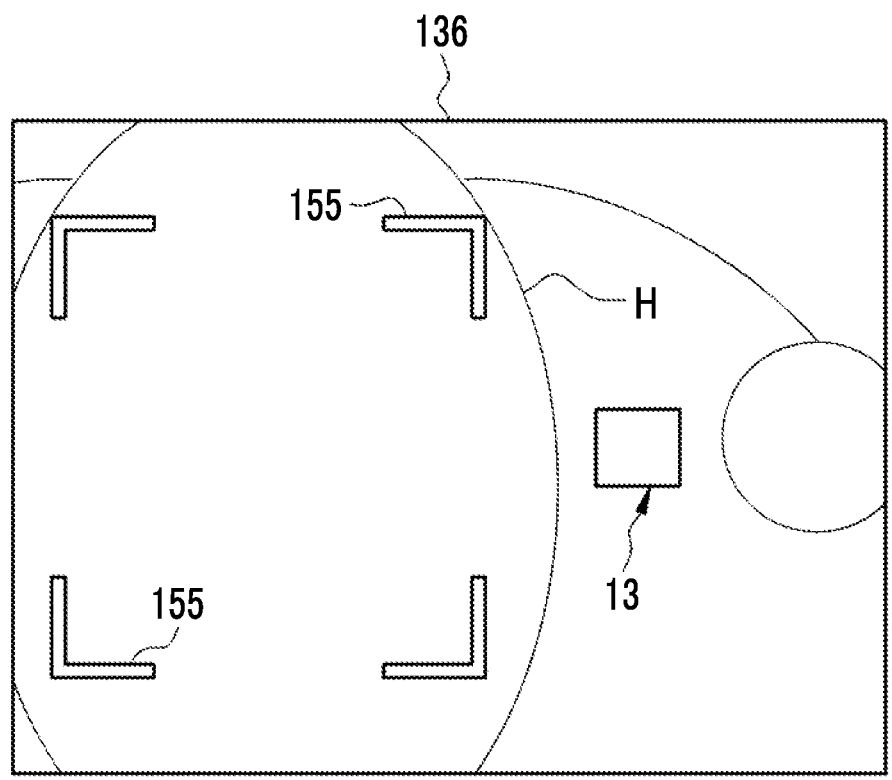
FIG. 26 is a diagram illustrating another example of a cassette frame.

The index indicating the in-image cassette position is not limited to the cassette frame 135 obtained by connecting four corners of the front surface 85A with straight lines. As illustrated in FIG. 26, the index may be a cassette frame 155 in which four corners of the front surface 85A are represented by L-shaped lines.

In each of the above-described embodiments, for example, the hardware structures of the processing units performing various processes, such as the camera image acquisition unit 125, the position signal acquisition unit 126, the calculation unit 127, the composite image generation unit 128, and the display controller 129, are the following various processors.

Various processors include a CPU, a programmable logic device (PLD), and a dedicated electric circuit. The CPU is a general-purpose processor that executes software (program) to function as various processing units as it is known. The PLD is a processor whose circuit configuration can be changed after it is manufactured, such as a field programmable gate array (FPGA). The dedicated electric circuit is a processor having a dedicated circuit configuration designed to perform a specific process, such as an application specific integrated circuit (ASIC).

One processing unit may be one of the various processors or a combination of two or more processors of the same type or different types (for example, a combination of a plurality of FPGAs and a combination of a CPU and an FPGA). In addition, a plurality of processing units may be formed by one processor. As an example in which a plurality of processing units are formed by one processor, first, one processor is formed by a combination of one or more CPUs and software and the processor functions as the plurality of processing units. Second, a processor which is typified by a system-on-chip (SoC) and in which the overall function of a system including a plurality of processing units is implemented by one IC chip is used. As such, the hardware structure of various processing units is formed by one or more of the various processors.

In addition, specifically, the hardware structure of the various processors is an electric circuit (circuitry) which is a combination of circuit elements such as semiconductor elements.

A radiography system described in the following Supplementary Note 1 can be understood from the above description.

Supplementary Note 1

A radiography system includes: a radiation source that irradiates a subject with radiation; an electronic cassette that detects a radiographic image based on the radiation which has been transmitted through the subject; a camera image acquisition processor that acquires a camera image which is an optical image of at least the subject from a camera that is attached to the radiation source; a position signal acquisition processor that acquires a position signal indicating a position of a part of a peripheral portion of the electronic cassette which is disposed at a position facing the radiation source from a position detection unit that is operated in a state in which at least some components are disposed at an exposure position included in the camera image and in a field of view of the camera; a calculation processor that calculates an in-image cassette position which is a position of the electronic cassette in the camera image, on the basis of a position of the position detection unit in the camera image and the position signal; a composite image generation processor that generates a composite image of the camera image and an index indicating the in-image cassette position; and a display control processor that performs control for displaying the composite image on a display unit.

An electronic cassette positioning support apparatus described in the following Supplementary Notes 2 and 3, a method for operating an electronic cassette positioning support apparatus described in the following Supplementary Note 4, and a program for operating an electronic cassette positioning support apparatus described in the following Supplementary Note 5 can be understood from each of the above-described embodiments. In each of the above-described embodiments, the console 55 corresponds to the electronic cassette positioning support apparatus.

Supplementary Note 2

There is provided an electronic cassette positioning support apparatus that supports relative positioning between a subject and an electronic cassette which detects a radiographic image based on radiation that has been emitted from a radiation source and transmitted through the subject in a case in which the electronic cassette is used. The electronic cassette positioning support apparatus includes: a camera image acquisition unit that acquires a camera image which is an optical image of at least the subject from a camera that is attached to the radiation source; a position signal acquisition unit that acquire a position signal indicating a position of a part of a peripheral portion of the electronic cassette which is disposed at a position facing the radiation source from a position detection unit that is operated in a state in which at least some components are disposed at an exposure position included in the camera image and in a field of view of the camera; a calculation unit that calculates an in-image cassette position which is a position of the electronic cassette in the camera image, on the basis of a position of the position detection unit in the camera image and the position signal; a composite image generation unit that generates a composite image of the camera image and an index indicating the in-image cassette position; and a display controller that performs control for displaying the composite image on a display unit.

Supplementary Note 3

There is provided an electronic cassette positioning support apparatus that supports relative positioning between a subject and an electronic cassette which detects a radiographic image based on radiation that has been emitted from a radiation source and transmitted through the subject in a case in which the electronic cassette is used. The electronic cassette positioning support apparatus includes: a camera image acquisition unit that acquires a camera image which is an optical image of at least the subject from a camera that is attached to the radiation source; a position signal acquisition unit that acquire a position signal indicating a position of a part of a peripheral portion of the electronic cassette which is disposed behind the back of the subject as viewed from the radiation source from a position detection unit that is operated in a state in which at least some components are disposed at an exposure position included in the camera image and in a field of view of the camera; a calculation unit that calculates an in-image cassette position which is a position of the electronic cassette in the camera image, on the basis of a position of the position detection unit in the camera image and the position signal; a composite image generation unit that generates a composite image of the camera image and an index indicating the in-image cassette position; and a display controller that performs control for displaying the composite image on a display unit.

Supplementary Note 4

There is provided a method for operating an electronic cassette positioning support apparatus that supports relative positioning between a subject and an electronic cassette which detects a radiographic image based on radiation that has been emitted from a radiation source and transmitted through the subject in a case in which the electronic cassette is used. The method for operating an electronic cassette positioning support apparatus includes: a camera image acquisition step of acquiring a camera image which is an optical image of at least the subject from a camera that is attached to the radiation source; a position signal acquisition step of acquiring a position signal indicating a position of a part of a peripheral portion of the electronic cassette which is disposed at a position facing the radiation source from a position detection unit that is operated in a state in which at least some components are disposed at an exposure position included in the camera image and in a field of view of the camera; a calculation step of calculating an in-image cassette position which is a position of the electronic cassette in the camera image, on the basis of a position of the position detection unit in the camera image and the position signal; a composite image generation step of generating a composite image of the camera image and an index indicating the in-image cassette position; and a display control step of performing control for displaying the composite image on a display unit.

Supplementary Note 5

There is provided a program for operating an electronic cassette positioning support apparatus that supports relative positioning between a subject and an electronic cassette which detects a radiographic image based on radiation that has been emitted from a radiation source and transmitted through the subject in a case in which the electronic cassette is used. The program for operating the electronic cassette positioning support apparatus causes a computer to perform: a camera image acquisition function of acquiring a camera image which is an optical image of at least the subject from a camera that is attached to the radiation source; a position signal acquisition function of acquiring a position signal indicating a position of a part of a peripheral portion of the electronic cassette which is disposed at a position facing the radiation source from a position detection unit that is operated in a state in which at least some components are disposed at an exposure position included in the camera image and in a field of view of the camera; a calculation function of calculating an in-image cassette position which is a position of the electronic cassette in the camera image, on the basis of a position of the position detection unit in the camera image and the position signal; a composite image generation function of generating a composite image of the camera image and an index indicating the in-image cassette position; and a display control function of performing control for displaying the composite image on a display unit.

In each of the above-described embodiments, the case in which the operator OP moves the treatment cart 11 to the hospital room and performs free imaging has been described as an example. However, the invention can also be applied to a case in which the operator OP performs free imaging in the imaging room using an X-ray generation apparatus installed in the imaging room.

The invention is not limited to the X-rays and can also be applied to a case in which other types of radiation including γ-rays are used.

The invention is not limited to each of the above-described embodiments and can adopt various configurations without departing from the scope and spirit of the invention. In addition, the invention can be applied to a program and a storage medium storing the program.

EXPLANATION OF REFERENCES

10: X-ray imaging system (radiography system)
11: treatment cart
12: electronic cassette
13, 142, 151A, 151B: position detection unit
14: bed
20: axle unit
21: main body unit
22: support
23: arm
24: X-ray source (radiation source)
25: caster
26: handle
27: cassette slot
28: unit accommodation unit
29: support arm
30: charging unit
31: touch panel display (touch panel, display unit)
35: first support
36: second support
40: X-ray tube
41: irradiation field limiter
42: irradiation switch
45: camera attachment unit
46: camera
50: voltage generation unit
51: controller
52: wireless communication unit
53: wired communication unit
54: storage device (storage)
55: console
60: image sensor
61: wireless transmission unit
62: battery
65: imaging order
68: menu and condition table
70: cassette registration table
72: X-ray image (radiographic image)
73: image file
74: accessory information
78: order management list
80: sensor panel
81: circuit unit
85: housing
85A: front surface (irradiation surface)
85B: rear surface
85C: side surface
86: transmission plate
87: scintillator
88: optical detection substrate
120: camera image
123: operation program
125: camera image acquisition unit
126: position signal acquisition unit
127: calculation unit
128: composite image generation unit
129: display controller
135, 155: cassette frame (index)
136: composite image 140, 140A to 140C: electromagnetic wave generation source
141: electromagnetic wave detection sensor
150: time-of-flight camera
H: subject
OP: operator
XC, YC, ZC: camera coordinate system
FOV: field of view of camera
P1 to P4: corner of front surface (irradiation surface)
P5: corner of rear surface
XU, YU, ZU: unit coordinate system
RA: roll axis
α: rotation angle of electronic cassette on roll axis
YA: yaw axis
β: rotation angle of electronic cassette on yaw axis
PA: pitch axis
γ: rotation angle of electronic cassette on pitch axis
LXZ23: line connecting corners P2 and P3 in XUZU plane
LYZ25: line connecting corners P2 and P5 in YUZU plane
LXY23: line connecting corners P2 and P3 in XUYU plane
TM: coordinate transformation matrix
ST100 to ST140, ST1101 to ST1105: step

What is claimed is:

1. A radiography system comprising:
a radiation source that irradiates a subject with radiation;
an electronic cassette that detects a radiographic image based on the radiation which has been transmitted through the subject;
a camera that is attached to the radiation source and outputs a camera image which is an optical image of at least the subject;
a position detection unit that outputs a position signal indicating a position of a part of a peripheral portion of the electronic cassette which is disposed at a position facing the radiation source and operates in a state in which at least some components are disposed at an exposure position included in the camera image and in a field of view of the camera;
a calculation unit that calculates an in-image cassette position which is a position of the electronic cassette in the camera image, on the basis of a position of the position detection unit in the camera image and the position signal;
a composite image generation unit that generates a composite image of the camera image and an index indicating the in-image cassette position; and
a display controller that performs control for displaying the composite image on a display unit,
wherein the position detection unit includes an electromagnetic wave generation source that generates an electromagnetic wave and an electromagnetic wave detection sensor that is attached to a predetermined position of the electronic cassette and detects the electromagnetic wave.

2. The radiography system according to claim 1,
wherein the component disposed at the exposure position is the electromagnetic wave generation source.

3. The radiography system according to claim 1,
wherein the electromagnetic wave generation source is a magnetic field generation source or a radio wave generation source, and
the electromagnetic wave detection sensor is a magnetic detection sensor or a radio wave detection sensor.

4. A radiography system comprising:
a radiation source that irradiates a subject with radiation;
an electronic cassette that detects a radiographic image based on the radiation which has been transmitted through the subject;
a camera that is attached to the radiation source and outputs a camera image which is an optical image of at least the subject;
a position detection unit that outputs a position signal indicating a position of a part of a peripheral portion of the electronic cassette which is disposed at a position facing the radiation source and operates in a state in which at least some components are disposed at an exposure position included in the camera image and in a field of view of the camera;
a calculation unit that calculates an in-image cassette position which is a position of the electronic cassette in the camera image, on the basis of a position of the position detection unit in the camera image and the position signal;
a composite image generation unit that generates a composite image of the camera image and an index indicating the in-image cassette position; and
a display controller that performs control for displaying the composite image on a display unit,
wherein the position detection unit comprises a wireless transmission unit that wirelessly transmits the position signal and a battery that supplies power to each unit including the wireless transmission unit and is wirelessly operated.

5. The radiography system according to claim 4,
wherein the calculation unit calculates, as the in-image cassette position, positions of four corners of an irradiation surface which is irradiated with the radiation in the electronic cassette.

6. The radiography system according to claim 5,
wherein the composite image generation unit combines, as the index, a frame that is formed by connecting the positions of the four corners with straight lines.

7. The radiography system according to claim 5,
wherein the calculation unit calculates a coordinate transformation matrix for transforming a unit coordinate system which is a coordinate system of the position detection unit into a camera coordinate system which is a coordinate system of the camera from the position of the position detection unit in the camera image, and
the calculation unit calculates coordinates of the in-image cassette position represented by the camera coordinate system from the coordinate transformation matrix and coordinates of the positions of the four corners of the irradiation surface represented by the unit coordinate system.

8. The radiography system according to claim 7,
wherein the calculation unit calculates the coordinate transformation matrix from a direction and size of the position detection unit in the camera image in addition to the position of the position detection unit in the camera image.

9. The radiography system according to claim 7,
wherein the calculation unit detects a specific position of a side surface of the electronic cassette in the unit coordinate system from the position signal and calculates the positions of the four corners of the irradiation surface on the basis of the detected specific position.

10. The radiography system according to claim 9,
wherein the position detection unit includes an image sensor that outputs, as the position signal, a two-dimensional image of a part of the peripheral portion of the electronic cassette.

11. The radiography system according to claim 10,
wherein the calculation unit detects at least three positions as the specific position and calculates a rotation angle of the electronic cassette on the basis of the detected at least three positions.

12. The radiography system according to claim 10,
wherein the component disposed at the exposure position is the image sensor.

13. The radiography system according to claim 10,
wherein the image sensor is any one of an optical camera, a time-of-flight camera, an ultrasound sensor, and a radar sensor.

14. The radiography system according to claim 4,
wherein a plurality of types of position detection units having different types of sensors outputting the position signal are prepared.

15. The radiography system according to claim 4,
wherein a plurality of position detection units which are of the same type and have the same type of sensors outputting the position signal are prepared.

16. A radiography system comprising:
a radiation source that irradiates a subject with radiation;
an electronic cassette that detects a radiographic image based on the radiation which has been transmitted through the subject;
a camera that is attached to the radiation source and outputs a camera image which is an optical image of at least the subject;
a position detection unit that outputs a position signal indicating a position of a part of a peripheral portion of the electronic cassette which is disposed at a position facing the radiation source and operates in a state in which at least some components are disposed at an exposure position included in the camera image and in a field of view of the camera;
a calculation unit that calculates an in-image cassette position which is a position of the electronic cassette in the camera image, on the basis of a position of the position detection unit in the camera image and the position signal;
a composite image generation unit that generates a composite image of the camera image and an index indicating the in-image cassette position;
a display controller that performs control for displaying the composite image on a display unit; and
a unit accommodation unit that detachably accommodates the position detection unit.

17. The radiography system according to claim 16,
wherein, in a case in which the position detection unit is detached from the unit accommodation unit, the position detection unit is operated.

18. The radiography system according to claim 16,
wherein the position detection unit comprises a wireless transmission unit that wirelessly transmits the position signal and a battery that supplies power to each unit including the wireless transmission unit and is wirelessly operated, and
wherein the unit accommodation unit comprises a charging unit that charges the battery.

19. A method for operating a radiography system comprising a radiation source that irradiates a subject with radiation and an electronic cassette that detects a radiographic image based on the radiation transmitted through the subject, the method comprising:
a camera image acquisition step of acquiring a camera image which is an optical image of at least the subject from a camera that is attached to the radiation source;
a position signal acquisition step of acquiring a position signal indicating a position of a part of a peripheral portion of the electronic cassette which is disposed at a position facing the radiation source from a position detection unit that is operated in a state in which at least some components are disposed at an exposure position included in the camera image and in a field of view of the camera;
a calculation step of calculating an in-image cassette position which is a position of the electronic cassette in the camera image, on the basis of a position of the position detection unit in the camera image and the position signal;
a composite image generation step of generating a composite image of the camera image and an index indicating the in-image cassette position; and
a display control step of performing control for displaying the composite image on a display unit,
wherein acquiring the position signal includes generating an electromagnetic wave and, using an electromagnetic wave detection sensor that is attached to a predetermined position of the electronic cassette, detecting the electromagnetic wave.

20. A method for operating a radiography system comprising a radiation source that irradiates a subject with radiation and an electronic cassette that detects a radiographic image based on the radiation transmitted through the subject, the method comprising:
a camera image acquisition step of acquiring a camera image which is an optical image of at least the subject from a camera that is attached to the radiation source;
a position signal acquisition step of acquiring a position signal indicating a position of a part of a peripheral portion of the electronic cassette which is disposed at a position facing the radiation source from a position detection unit that is operated in a state in which at least some components are disposed at an exposure position included in the camera image and in a field of view of the camera;
a calculation step of calculating an in-image cassette position which is a position of the electronic cassette in the camera image, on the basis of a position of the position detection unit in the camera image and the position signal;
a composite image generation step of generating a composite image of the camera image and an index indicating the in-image cassette position; and
a display control step of performing control for displaying the composite image on a display unit,
wherein acquiring the position signal includes wirelessly transmitting the position signal via a wireless transmission unit and supplying power, via a battery, to the wireless transmission unit, the position detection unit being wirelessly operated.

21. A method for operating a radiography system comprising a radiation source that irradiates a subject with radiation and an electronic cassette that detects a radiographic image based on the radiation transmitted through the subject, the method comprising:
a camera image acquisition step of acquiring a camera image which is an optical image of at least the subject from a camera that is attached to the radiation source;
a position signal acquisition step of acquiring a position signal indicating a position of a part of a peripheral portion of the electronic cassette which is disposed at a position facing the radiation source from a position detection unit that is operated in a state in which at least some components are disposed at an exposure position included in the camera image and in a field of view of the camera;
a calculation step of calculating an in-image cassette position which is a position of the electronic cassette in the camera image, on the basis of a position of the position detection unit in the camera image and the position signal;
a composite image generation step of generating a composite image of the camera image and an index indicating the in-image cassette position;
a display control step of performing control for displaying the composite image on a display unit; and
detachably accommodating the position detection unit via a unit accommodation unit.

* * * * *